United States Patent
Spargo et al.

(10) Patent No.: US 10,463,665 B2
(45) Date of Patent: Nov. 5, 2019

(54) SALT OF A PYRIMIDO[6,1-A]ISOQUINOLIN-4-ONE COMPOUND

(71) Applicant: VERONA PHARMA PLC, Cardiff (GB)

(72) Inventors: Peter Lionel Spargo, Canterbury (GB); Edward James French, Canterbury (GB); Julian Scott Northen, South Shields (GB); John Mykytiuk, Houghton-le-Spring (GB)

(73) Assignee: VERONA PHARMA PLC, Cardiff (GB)

( * ) Notice: Subject to any disclaimer, the term of this patent is extended or adjusted under 35 U.S.C. 154(b) by 0 days.

(21) Appl. No.: 15/549,500

(22) PCT Filed: Feb. 10, 2016

(86) PCT No.: PCT/GB2016/050313
§ 371 (c)(1),
(2) Date: Aug. 8, 2017

(87) PCT Pub. No.: WO2016/128742
PCT Pub. Date: Aug. 18, 2016

(65) Prior Publication Data
US 2018/0021337 A1    Jan. 25, 2018

(30) Foreign Application Priority Data
Feb. 11, 2015    (GB) .................................. 1502260.1

(51) Int. Cl.
*A61K 31/513*    (2006.01)
*A61K 9/00*    (2006.01)
(Continued)

(52) U.S. Cl.
CPC .......... *A61K 31/513* (2013.01); *A61K 9/0075* (2013.01); *A61K 31/185* (2013.01);
(Continued)

(58) Field of Classification Search
CPC ........................... C07D 239/00; C07D 487/00
See application file for complete search history.

(56) References Cited

U.S. PATENT DOCUMENTS 4,581,172 A    4/1986 Kaiser et al.
5,141,936 A    8/1992 Rupp et al.
(Continued)

FOREIGN PATENT DOCUMENTS

WO    00/58308    10/2000
WO    03/105902 A1    12/2003
(Continued)

OTHER PUBLICATIONS

Gould, International Journal of Pharmaceutics,1986;33:201-217.*
(Continued)

*Primary Examiner* — San Ming R Hui
(74) *Attorney, Agent, or Firm* — MH2 Technology Law Group, LLP

(57) ABSTRACT

The present invention relates to a pharmaceutically acceptable acid addition salt of: (i) 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one (RPL554); and (ii) ethane-1,2-disulfonic acid, ethanesulfonic acid, methanesulfonic acid, benzenesulfonic acid, p-toluenesulfonic acid, hydrochloric acid, hydrobromic acid, phosphoric acid or sulfuric acid.

12 Claims, 8 Drawing Sheets

(51) Int. Cl.
*C07D 471/04* (2006.01)
*A61K 31/185* (2006.01)
*A61K 31/519* (2006.01)
*A61K 45/06* (2006.01)

(52) U.S. Cl.
CPC ............ *A61K 31/519* (2013.01); *A61K 45/06* (2013.01); *C07D 471/04* (2013.01); *A61K 2300/00* (2013.01)

(56) References Cited

U.S. PATENT DOCUMENTS

| | | |
|---|---|---|
| 6,794,391 B2 | 9/2004 | Oxford et al. |
| 7,105,663 B2 | 9/2006 | Oxford et al. |
| 7,378,424 B2 | 5/2008 | Oxford et al. |
| 8,242,127 B2 | 8/2012 | Oxford et al. |
| 9,062,047 B2 | 6/2015 | Walker et al. |
| 9,700,558 B2 | 7/2017 | Walker et al. |
| 9,717,732 B2 | 8/2017 | Walker et al. |
| 2003/0036542 A1 | 2/2003 | Oxford et al. |
| 2004/0171828 A1 | 9/2004 | Oxford et al. |
| 2004/0176353 A1 | 9/2004 | Oxford et al. |
| 2008/0206163 A1 | 8/2008 | Oxford et al. |
| 2013/0225616 A1 | 8/2013 | Walker et al. |
| 2016/0000790 A1 | 1/2016 | Walker et al. |
| 2016/0008363 A1 | 1/2016 | Walker et al. |
| 2017/0112839 A1 | 4/2017 | Abbott-Banner et al. |
| 2017/0239178 A1 | 8/2017 | Spargo et al. |

FOREIGN PATENT DOCUMENTS

| | | |
|---|---|---|
| WO | 2011/127586 A1 | 10/2011 |
| WO | 2012/020016 A1 | 2/2012 |
| WO | 2014/140647 A1 | 9/2014 |
| WO | 2014/140648 A1 | 9/2014 |
| WO | 2015/173551 A1 | 11/2015 |
| WO | 2016/042313 A1 | 3/2016 |

OTHER PUBLICATIONS

Badawy et al., Journal of PharmaceuticalScience, 2007; 96(5):948-959.*

Franciosi et al., "Efficacy and safety of RPL554, a dual PDE3 and PDE4 inhibitor, in healthy volunteers and in patients with asthma or chronic obstructive pulmonary disease: findings from four clinical trials", The Lancet. Respiratory Medicine, Nov. 2013, vol. 1, No. 9, pp. 714-727.

Search Report from UK Intellectual Property Office for Application No. GB1502260.1 dated Nov. 3, 2015, 6 pages.

Stahl et al., Handbook of Pharmaceutical Salts: Properties, Selection, and Use, 2002, VHCA, Zurich, Switzerland and Wiley-VCH, Weinheim, Germany.

* cited by examiner

SALT OF A PYRIMIDO[6,1-A]ISOQUINOLIN-4-ONE COMPOUND

CROSS-REFERENCE TO RELATED APPLICATIONS

This application is a U.S. National Stage application of PCT/GB2016/050313, filed 10 Feb. 2016, which claims priority to Great Britain Application No. 1502260.1, filed 11 Feb. 2015, the disclosures of which are hereby incorporated by reference in their entireties.

FIELD OF THE INVENTION

The present invention relates to salts of a pyrimido[6,1-A]isoquinolin-4-one compound and pharmaceutical compositions comprising these salts. Medical uses of such salts are also described.

BACKGROUND OF THE INVENTION

A number of factors must be considered when developing an appropriate form of an active pharmaceutical ingredient (API) for formulation for administration to human subjects. These include efficacy, toxicity, stability, solubility/dissolution and acidity/basicity. Different formulations comprising a number of different forms of the API are usually evaluated. The outcomes of such evaluations are unpredictable.

Solubility/dissolution, stability and acidity/basicity can be very important factors to control for an API. Solubility/dissolution must be at an appropriate level to enable delivery of a sufficient dose of the active ingredient to have the desired therapeutic effect in a patient. The solubilities of different salt forms of a therapeutic agent are unpredictable.

The stability of an API must be sufficient to ensure that the product is shelf stable for long periods. Acidity/basicity is of importance for orally administered drugs and inhaled drugs as overly acidic formulations may cause discomfort to subjects upon administration.

RPL554 (9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one) is a dual PDE3/PDE4 inhibitor and is described in WO 00/58308. As a combined PDE3/PDE4 inhibitor, RPL554 has both anti-inflammatory and bronchodilatory activity and is useful in the treatment of respiratory disorders such as asthma and chronic obstructive pulmonary disease (COPD). The structure of RPL554 is shown below.

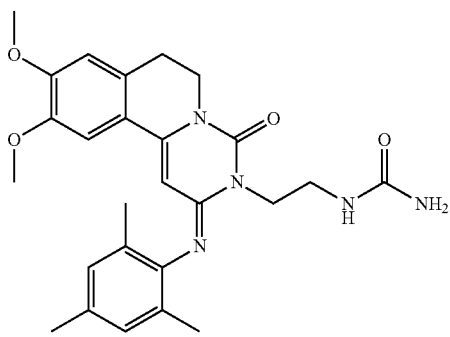 [SMILES: COc1cc2c(cc1OC)-c1c/c(=N\c3c(C)cc(C)cc3C)n(CCNC(N)=O)c(=O)n1CC2]

Owing to its applicability in the treatment of respiratory disorders, it is often preferable to administer RPL554 by inhalation. Franciosi et al. disclose a solution of RPL554 in a citrate-phosphate buffer at pH 3.2 (The Lancet: Respiratory Medicine November 2013; 1(9):714-27. DOI: 10.1016/S2213-2600(13)70187-5). The preparation of salts of RPL554 has not been described.

SUMMARY OF THE INVENTION

It is a finding of the present invention that certain salts of RPL554 have highly desirable properties. In particular, specific pharmaceutically acceptable salts of RPL554 have been found to have improved water solubility and improved solubility in appropriately pH buffered solutions. The increased solubility in buffered solutions allows for higher drug loading in solutions of more mild pH, which could lead to greater tolerance of patients to inhalation or oral administration. Certain specific salts of RPL554 have also been found to be crystalline. Crystalline salts are typically more stable than amorphous forms, and are particularly desirable if the RPL554 is to be successfully delivered as a dry powder or in other formulations in which the active ingredient is present in the solid state.

Furthermore, certain salts of RPL554 have been found to have desirable intrinsic dissolution rates which can lead to improved bioavailability. Particular salts of RPL554 have also been found to be well suited to pressurised metered dose and dry powder formulations.

The thermal stabilities of certain salts of RPL554 have also been found to be better than the thermal stabilities of other salts. Such salts are desirable as they are resistant to variation in temperatures without changes in form. Stability to changes in humidity is also desirable.

Accordingly, the present invention provides a pharmaceutically acceptable acid addition salt of:
(i) 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one (RPL554); and
(ii) ethane-1,2-disulfonic acid, ethanesulfonic acid, methanesulfonic acid, benzenesulfonic acid, p-toluenesulfonic acid, hydrochloric acid, hydrobromic acid, phosphoric acid or sulfuric acid.

The invention further provides a pharmaceutical composition comprising a pharmaceutically acceptable acid addition salt of the invention and a pharmaceutically acceptable excipient, carrier or diluent.

The invention further provides a pharmaceutically acceptable acid addition salt of the invention for use in the treatment of the human or animal body.

The invention further provides a pharmaceutically acceptable acid addition salt of the invention for use in the treatment or prevention of a disease or condition selected from asthma, allergic asthma, hay fever, allergic rhinitis, bronchitis, emphysema, bronchiectasis, chronic obstructive pulmonary disease (COPD), adult respiratory distress syndrome (ARDS), steroid resistant asthma, severe asthma, paediatric asthma, cystic fibrosis, lung fibrosis, pulmonary fibrosis, interstitial lung disease, skin disorders, atopic dermatitis, psoriasis, ocular inflammation, cerebral ischaemia, inflammatory diseases and auto-immune diseases.

The invention further provides a method of treating or preventing a disease or condition selected from asthma, allergic asthma, hay fever, allergic rhinitis, bronchitis, emphysema, bronchiectasis, chronic obstructive pulmonary disease (COPD), adult respiratory distress syndrome (ARDS), steroid resistant asthma, severe asthma, paediatric asthma, cystic fibrosis, lung fibrosis, pulmonary fibrosis, interstitial lung disease, skin disorders, atopic dermatitis, psoriasis, ocular inflammation, cerebral ischaemia, inflammatory diseases and auto-immune diseases in a subject, which method comprises administering to said subject an effective amount of a pharmaceutically acceptable acid addition salt of the invention.

DETAILED DESCRIPTION OF THE INVENTION

Figure 1:
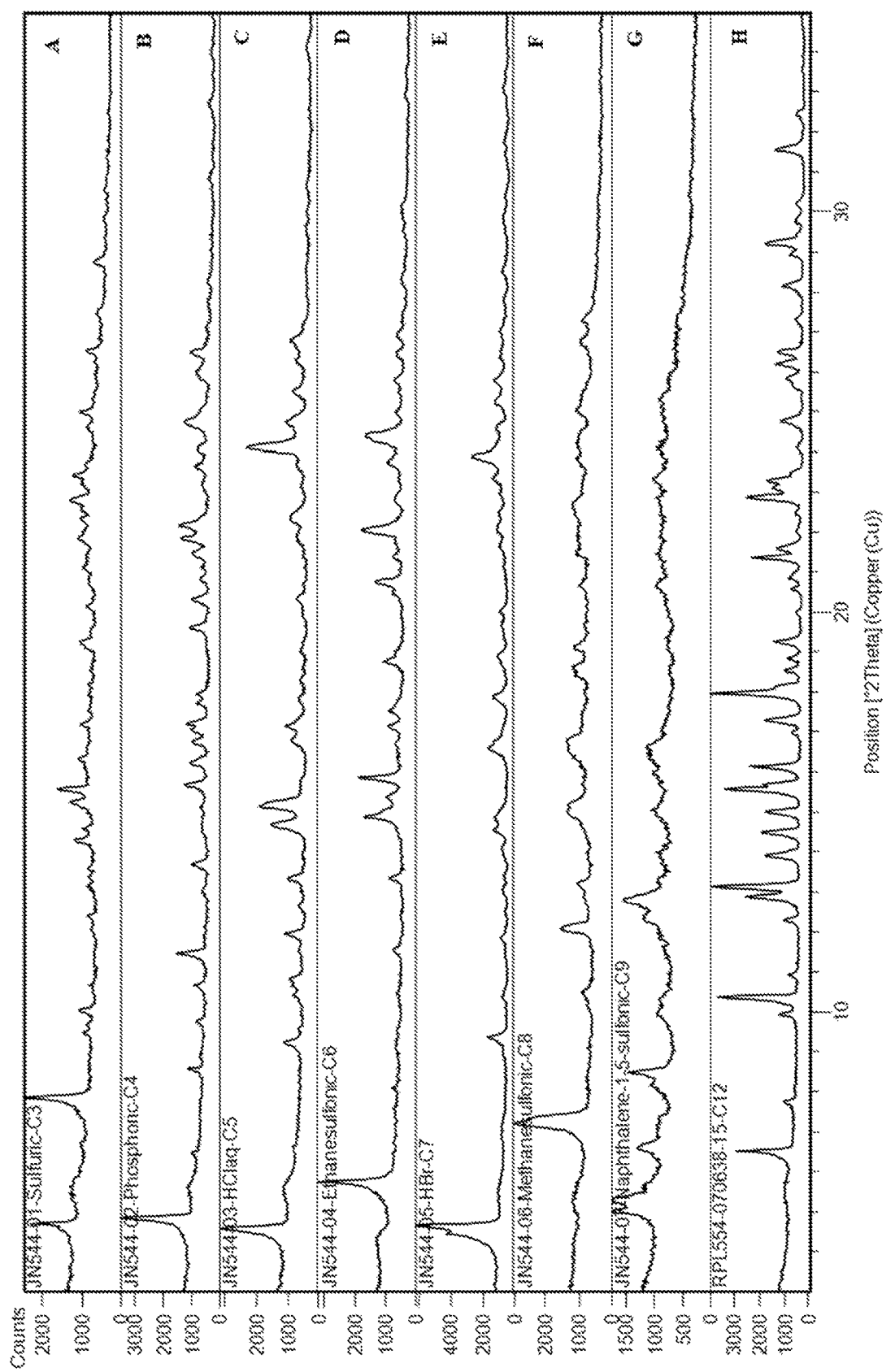
FIG. 1 shows XRPD patterns of solids isolated from RPL554 salt formation wherein the acid used is: sulfuric (A), phosphoric (B), hydrochloric-aqueous (C), ethanesulfonic (D), hydrobromic (E), methanesulfonic (F) and naphthalene-1,5-disulfonic (G). The XRPD pattern of the RPL554 free base is also shown (H).

The RPL554 salts of the invention are pharmaceutically acceptable acid addition salts of RPL554 and ethane-1,2-disulfonic acid, ethanesulfonic acid, methanesulfonic acid, benzenesulfonic acid, p-toluenesulfonic acid, hydrochloric acid, hydrobromic acid, phosphoric acid or sulfuric acid, or solvates thereof.

Typically, the acid is ethane-1,2-disulfonic acid, ethanesulfonic acid, methanesulfonic acid, benzenesulfonic acid, hydrochloric acid, or sulfuric acid.

An acid addition salt of RPL554 is a salt formed by reaction of RPL554 with an acid. RPL554 is weakly basic compound and may be protonated to form a cationic species which forms a salt with the conjugate base of the acid used.

The acid addition salt of RPL554 may be selected from RPL554 ethane-1,2-disulfonate, RPL554 ethanesulfonate, RPL554 methanesulfonate, RPL554 benzenesulfonate, RPL554 p-toluenesulfonate, RPL554 hydrochloride, RPL554 hydrobromide, RPL554 phosphate, RPL554 sulfate and solvates thereof. Typically, the salt is selected from RPL554 ethane-1,2-disulfonate, RPL554 phosphate, RPL554 methanesulfonate, RPL554 hydrochloride, RPL554 sulfate, and solvates thereof.

Solvates of salts are solid salts which comprise molecules of solvent. The solvent may be any solvent but is often water or an alcohol such as ethanol. The solvate may therefore be a hydrate or an alcoholate such as an ethanolate. The RPL554 salts may be anhydrates, monohydrates, dihydrates or higher hydrates, or non-stoichiometric hydrates.

The stoichiometry of the salts may be one to one, or it may be two to one, or one to two, or indeed any other ratio of acid to base.

The salt of the invention may for instance be RPL554 ethane-1,2-disulfonate or a solvate thereof. The stoichiometry of the RPL554 ethane-1,2-disulfonate salt is typically about 2:1 API:counter ion. The salt of the invention may for instance be RPL554 phosphate or a solvate thereof. The stoichiometry of the RPL554 phosphate salt is typically about 1:1 API:counter ion. The salt of the invention may for instance be RPL554 methanesulfonate or a solvate thereof. The stoichiometry of the RPL554 methanesulfonate salt is typically about 1:1 API:counter ion. The salt of the invention may for instance be RPL554 hydrochloride or a solvate thereof. The stoichiometry of the RPL554 hydrochloride salt is typically about 1:1 API:counter ion. The salt of the invention may for instance be RPL554 sulfate or a solvate thereof. The stoichiometry of the RPL554 sulfate salt is typically about 1:1 API:counter ion.

The stoichiometry of the salts can be determined by techniques known to those skilled in the art, such as $^1$H NMR.

The salts of the invention may be produced by any suitable method for producing salts of active pharmaceutical molecules. Typically, the salts are produced by dissolving RPL554 in a solvent, for instance dichloromethane or dimethylformamide, and subsequently adding a solution of the desired acid, for instance a solution of the acid in ethanol or THF. The salt may then be isolated by filtration, or by removing the solvent from the resulting composition, for instance by drying under vacuum. The salt concentrate may be subsequently triturated with an antisolvent, for example methyl tert-butyl ether and collected by filtration, or it may be purified and isolated by other means.

The RPL554 salt of the invention typically has a purity of greater than or equal to about 90%, greater than or equal to about 95% or greater than or equal to about 97%. The percentage may be calculated as area % based on HPLC separation. Thus, the invention provides a solid composition comprising greater than or equal to about 90%, greater than or equal to about 95%, or greater than or equal to about 97%, of a salt of RPL554 as defined herein.

The pharmaceutical composition according to the invention comprises a pharmaceutically acceptable acid addition salt as defined herein and a pharmaceutically acceptable excipient, carrier or diluent. The pharmaceutically acceptable excipient, carrier or diluent may be any suitable pharmaceutically acceptable excipient, carrier or diluent. These are well known to the skilled person.

The diluent may be any pharmaceutically acceptable diluent. The diluent is typically suitable for administration by inhalation. Examples of suitable diluents include water, ethanol and glycerol. The diluent is preferably water. The diluent is preferably sterile. The diluent may alternatively be selected from solid diluents such as lactose, dextrose, saccharose, cellulose, corn starch and potato starch. The diluent may contain buffer components to control the pH. The buffers may be derived from phosphate, citrate or acetate. The diluent may also contain sodium chloride.

The pharmaceutical composition may comprise for instance: lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Compositions which are liquid dispersions for oral administration may be syrups, emulsions and suspensions. The syrups may contain as carriers, for example, saccharose or saccharose with glycerine and/or mannitol and/or sorbitol.

Compositions which are suspensions or emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion, or for inhalation, may contain as carrier, for example, sterile water or preferably they may be in the form of sterile, aqueous, isotonic saline solutions.

Preferably, the composition of the invention is formulated for administration by inhalation.

The pharmaceutical composition may be a dry powder. Typically, a pharmaceutical composition which is a dry powder is delivered using a dry powder inhaler.

Typically, the dry powder inhaler is a Clickhaler, Novolizer, Certihaler, Diskus, Multihaler, Gyrohaler (Vectura Group plc), Aerolizer, Handihaler or Tubospin (PH&T S.p.A.), Acu-Breathe unit (Respirics, Inc.), Conix (Cambridge Consultants Limited), Miat Monohaler (Cyclohaler), Eclipse (Sanofi-Aventis), e-flex (Microdrug AG), Flowcaps (Hovione), Prohaler (Valois Pharm), DirectHaler (Trimel BioPharma), Single Dose SDD (Manta technologies), Monodose (Miat SpA), TwinCaps (Hovione), GenX (CCL), SkyeHaler (SkyePharma), EasyHaler (Orion Pharma), or Taifun (Akela Pharma Inc.), with Clickhaler, Novolizer, Diskus and Aerolizer being the preferred dry powder inhalers.

Typically, a pharmaceutical composition which is a dry powder is prepared by milling, spray drying, fluidized spray drying, spray congealing, micronization, controlled crystallization, co-crystallization, ultrasound assisted crystallization, freeze drying or particle precipitation of the salt. Typically, the resulting powder has a particle size with a mass median aerodynamic diameter from about 1 μm to about 10 μm, preferably from about 3.5 μm to about 10 μm, more preferably from about 4 μm to about 5.5 μm, or from about 5 μm to about 10 μm, or from about 5.5 μm to about 10 μm or from about 6 μm to about 10 μm. The resulting powder may instead have a particle size with a mass median aerodynamic diameter from about 2 μm to about 5 μm, for instance from 2.5 μm to about 4.5 μm.

A dry powder pharmaceutical composition may comprise (a) from 50.0 to 99.8 wt % lactose powder and (b) from 0.2 to 50.0 wt % of a salt of RPL554 according to the invention. A preferred dry powder pharmaceutical composition comprises (a) from 80.0 to 99.8 wt % lactose powder and (b) from 0.2 to 20.0 wt % of a salt of RPL554 according to the invention. For instance, the powder pharmaceutical composition may comprise (a) from 95.0 to 99.8 wt % lactose powder and (b) from 0.2 to 5.0 wt % of a salt of RPL554 according to the invention. In some cases, the content of the salt may be approximately 1.0 wt %. For example, the powder pharmaceutical composition may comprise (a) from 99.2 to 99.8 wt % lactose powder and (b) from 0.2 to 0.8 wt % of a salt of RPL554 according to the invention.

In some cases, the pharmaceutical composition suitable for inhalation is in the form of a composition for a pressurised metered dose inhaler (pMDI). The pharmaceutical composition for administration by pMDI may comprise (a) a salt of RPL554 as defined herein and (b) one or more propellants. The one or more propellants are typically selected from hydrofluoroalkanes such as HFA 134a and HFA 227a. The formulation may further comprise (c) ethanol. The formulation may further comprise (d) a surfactant, for instance Tween 80. For example, the pharmaceutical composition may comprise (a) from 0.1 to 1.0 wt % of a salt of RPL554 as defined herein, (b) from 80.0 to 99.9 wt % of a hydrofluoroalkane, (c) from 0.0 to 19.0 wt % ethanol and (d) from 0.0 to 0.5 wt % Tween 80. In one embodiment, the pharmaceutical composition comprises (a) from 0.1 to 0.9 wt % of a salt of RPL554 as defined herein and (b) from total of HFA 134a and/or HFA 227a. Alternatively, the pharmaceutical composition may comprise (a) from 0.1 to 0.9 wt % of a salt of RPL554 as defined herein, (b) from 88.0 to 90.0 wt % total of HFA 134a and/or HFA 227a, (d) from 0.05 to 0.15 wt % of Tween 80 and (c) ethanol to balance.

In some cases, the pharmaceutical composition is an aqueous solution. Thus, the pharmaceutical composition is typically obtainable by dissolving a pharmaceutically acceptable salt of the invention in an aqueous solution. Dissolving the salt may comprise adding a solid form of the salt to the aqueous solution and agitating the resulting mixture to dissolve at least part of the salt. The resulting mixture may be heated to improve dissolution. pH may also be adjusted appropriately.

The concentration of the salt of the invention in the composition which is an aqueous solution is typically greater than or equal to about 0.1 mg/ml, greater than or equal to about 1 mg/ml or greater than or equal to about 2.5 mg/ml. For instance, the concentration of the salt of the invention in the aqueous solution is typically from about 1 mg/ml to about 50 mg/ml, for instance from about 2 mg/ml to 25 mg/ml or from about 2.5 mg/ml to 10 mg/ml.

Typically, the pharmaceutical composition which is an aqueous solution further comprises one or more buffers. The buffers are pharmaceutically acceptable buffers. Thus, the aqueous solution may be a buffered aqueous solution. The pharmaceutical composition may for instance be obtainable by dissolving the salt in a buffered aqueous solution. The buffers may be any buffers suitable for use in pharmaceutical composition, for instance a pharmaceutical invention suitable for inhalation. The one or more buffers are typically selected from acetate, citrate or phosphate buffers. The buffered aqueous solution typically comprises a phosphate buffer and/or a citrate buffer (for instance a citro-phosphate buffer). Citrate buffers include citric acid, sodium citrate and mixtures thereof. Phosphate buffers include phosphoric acid, monosodium phosphate, dibasic sodium phosphate and mixtures thereof. Acetate buffers include acetic acid and salts of acetic acid.

The pH of the buffered aqueous solution in the absence of RPL554 salt is typically from about 3.0 to about 7.0, for instance from about 4.0 to about 5.0. Formation of a pharmaceutical composition by dissolving a salt in the buffered aqueous solution may cause the pH of the buffered solution to vary. For instance, the pH may decrease on dissolution of the salt. This variation is typically small, however.

The pH of the pharmaceutical composition obtainable by dissolving the salt in an aqueous solution (e.g. a buffered aqueous solution) is typically greater than or equal to about 2.0. For instance, the pH of the pharmaceutical composition may be greater than or equal to about 3.0 or greater than or equal to about 4.0. The pH of the composition may be from about 3.0 to about 6.0, or from about 3.5 to about 5.5.

The aqueous solution may be a saline solution or a buffered saline solution. The aqueous solution may comprise from about 0.1 to about 2.0 w/w % saline (i.e. NaCl).

The pharmaceutical formulation may be a liquid pharmaceutical composition suitable for administration by inhalation comprising a diluent and a suspension of particles of a salt of RPL554 as described herein. The suspended particles of the salt of RPL554 typically have a particle size distribution with a Dv50 (median particle size by volume) value of from about 0.2 μm to about 5 μm. The Dv50 may be as measured using laser diffraction. The diluent may be water or a hydrofluoroalkane. The liquid pharmaceutical composition may further comprise a buffer, a solvent such as ethanol or a surfactant such as Tween (e.g. Tween 20 or 80).

The invention also provides a nebulizer comprising a pharmaceutical composition according to the invention which is an aqueous solution. The nebulizer is typically loaded with the pharmaceutical composition. The nebulizer typically comprises from about 1 mL to about 200 mL, more typically from 1 mL to 20 mL of the liquid pharmaceutical composition.

Nebulizers use compressed air to aerosolise a liquid pharmaceutical composition into an aerosol that is inhaled into a subject's respiratory tract. Examples of nebulizers include a soft mist nebulizer, a vibrating mesh nebulizer, a jet nebulizer and an ultrasonic wave nebulizer. Suitable nebulizer devices include the Philips I-Neb™ (Philips), the Pan LC Sprint (Pari GmbH), the AERx® Pulmonary Delivery System (Aradigm Corp.) and the Pari LC Plus Reusable Nebulizer (Pari GmbH).

The nebulizer is typically able to aerosolize the RPL554 salt solution into an aerosol comprising particles with an MMAD of from about 1 to about 10 μm, preferably from about 3 μm to about 10 μm, more preferably from about 4 μm to about 5.5 μm, or from about 5 μm to about 10 μm, or from about 5.5 μm to about 10 μm or from about 6 μm to about 10 μm. The MMAD may be from about 2 μm to about 5 μm, for instance from 2.5 μm to about 4.5 μm.

The invention also provides a pharmaceutically acceptable acid addition salt as defined herein for use in the treatment of the human or animal body. The invention also provides a pharmaceutical combination as defined herein for use in the treatment of the human or animal body.

Treatment of the human or animal body typically comprises the treatment or prevention of a disease or condition selected from asthma, allergic asthma, hay fever, allergic rhinitis, bronchitis, emphysema, bronchiectasis, chronic obstructive pulmonary disease (COPD), adult respiratory distress syndrome (ARDS), steroid resistant asthma, severe asthma, paediatric asthma, cystic fibrosis, lung fibrosis, pulmonary fibrosis, interstitial lung disease, skin disorders, atopic dermatitis, psoriasis, ocular inflammation, cerebral ischaemia, inflammatory diseases and auto-immune diseases.

Often, the disease or condition is asthma or chronic obstructive pulmonary disease (COPD).

The invention also provides a method of treating or preventing a disease or condition as defined herein in a subject, which method comprises administering to said subject an effective amount of a pharmaceutically acceptable acid addition salt of the invention.

An effective amount of RPL554 is typically from about 0.001 mg/kg to 50 mg/kg for a single dose. An effective amount of RPL554 is often from about 0.001 mg/kg to 1 mg/kg for a single dose. For instance, an effective amount may be a dose of from about 0.01 mg to about 500 mg, or from about 0.01 mg to 100 mg, preferably from about 0.1 mg to about 6 mg. A single dose of RPL554 may be from 0.05 mg to 5 mg or from 0.5 mg to 3 mg, for instance about 1.5 mg. Doses may be administered daily. For instance, the dose of RPL554 may be from 0.001 mg/kg/day to 50 mg/kg/day, typically from 0.001 mg/kg/day to 10 mg/kg/day or from 0.01 mg/kg/day to 1 mg/kg/day. These doses are typically the nominal dose charged to the inhaler. The liquid pharmaceutical composition may be administered once, twice or three times a day, or may be administered twice, three times, four times or five times a week. The composition may be administered as often as required by the patient.

The invention also provides the use of a pharmaceutically acceptable acid addition salt as defined herein in the manufacture of a medicament for the treatment of a disease or condition as defined herein.

The following Examples illustrate the invention.

EXAMPLES

Initial Investigations
Instruments and Methods

Automated counter ion screening—Counter ion screening of the API was performed using a Crissy platform supplied by Zinsser Analytic using Zinsser control software version 7.0.9. The Crissy platform was used to dispense stock solutions of API, counter ions and solvents followed by mixture agitation by vortex shaking. A 48 position block format for sample tubes was utilised for the screen which was conducted at ambient temperature. Sample tubes containing solids of interest were isolated by filtration and dried in vacuo at ambient temperature.

HPLC Conditions—RPL554 Chemical Purity by HPLC

Diluent Preparation—deionised water: acetonitrile (1:1). Both were mixed thoroughly and allowed to reach room temperature before use.

Blank Solution—the blank solution consists of diluent.

Sample Solution Preparation—Approximately 7 mg of sample was accurately weighed into a 14 ml glass vial and dissolved in approximately 14 ml of diluent, mix thoroughly and use these solutions for injection.

Column: X-Bridge Phenyl 150×4.6 mm, 3.5 µm particle size (Ex-Waters, part number 186003355); Mobile Phase: A—Purified Water: Trifluoroacetic Acid (100:0.1); B—Acetonitrile: Trifluoroacetic Acid (100:0.1); Flow Rate: 1.0 ml·min$^{-1}$; Injection Volume: 10 µl; Detection: UV @ 254 nm; Column Temperature: 30° C.; Post Run: 5 min

|  | Time (min) | % A | % B |
|---|---|---|---|
| Gradient: | 0 | 95 | 5 |
|  | 2 | 95 | 5 |
|  | 15 | 5 | 95 |
|  | 20 | 5 | 95 |
|  | 22 | 95 | 5 |

Expected retention time for RPL554: 11.3 minutes

Solution proton NMR—$^1$H NMR spectra were collected using a JEOL EX 270 MHz spectrometer equipped with an auto-sampler. The samples were dissolved in a suitable deuterated solvent for analysis. The data was acquired using Delta NMR Processing and Control Software version 4.3.

X-Ray Powder Diffraction (XRPD)—X-Ray Powder Diffraction patterns were collected on a PANalytical diffractometer using Cu Kα radiation (45 kV, 40 mA), 0-0 goniometer, focusing mirror, divergence slit (½"), soller slits at both incident and divergent beam (4 mm) and a PIXcel detector. The software used for data collection was X'Pert Data Collector, version 2.2f and the data was presented using X'Pert Data Viewer, version 1.2d. XRPD patterns were acquired under ambient conditions via a transmission foil sample stage (polyimide—Kapton, 12.7 µm thickness film) under ambient conditions using a PANalytical X'Pert PRO. The data collection range was 2.994-35° 2θ with a continuous scan speed of 0.202004° s$^{-1}$.

Differential Scanning calorimetry (DSC)—DSC data were collected on a PerkinElmer Pyris 4000 DSC equipped with a 45 position sample holder. The instrument was verified for energy and temperature calibration using certified indium. A predefined amount of the sample, 0.5-3.0 mg, was placed in a pin holed aluminium pan and heated at 20° C. min$^{-1}$ from 30 to 350° C., or varied as experimentation dictated. A purge of dry nitrogen at 60 ml·min$^{-1}$ was maintained over the sample. The instrument control, data acquisition and analysis were performed with Pyris Software v9.0.1.0203.

Thermo-Gravimetric Analysis (TGA)—TGA data were collected on a PerkinElmer Pyris 1 TGA equipped with a 20 position auto-sampler. The instrument was calibrated using a certified weight and certified Alumel and Perkalloy for temperature. A predefined amount of the sample, 1-5 mg, was loaded onto a pre-tared aluminium crucible and was heated at 20° C. min$^{-1}$ from ambient temperature to 400° C. A nitrogen purge at 20 ml·min$^{-1}$ was maintained over the sample. The instrument control, data acquisition and analysis were performed with Pyris Software v9.0.1.0203.

Water content by Karl Fischer titration—Approximately 0.2 g of sample was accurately weighed by difference and transferred into the Karl Fischer vessel. The sample was then mixed for 600 seconds to ensure that it was fully dissolved and then titrated against Hydranal Composite 5. Analysis was performed in duplicate.

Gravimetric Vapour Sorption—Sorption isotherms were obtained using a Hiden Isochema moisture sorption analyser (model IGAsorp), controlled by IGAsorp Systems Software V6.50.48. The sample was maintained at a constant temperature (25° C.) by the instrument controls. The humidity was controlled by mixing streams of dry and wet nitrogen, with a total flow of 250 ml·min$^{-1}$. The instrument was verified for relative humidity content by measuring three calibrated Rotronic salt solutions (10-50-88%). The weight change of the sample was monitored as a function of humidity by a microbalance (accuracy+/−0.005 mg). A defined amount of sample was placed in a tared mesh stainless steel basket under ambient conditions. A full experimental cycle typically consisted of three scans (sorption, desorption and sorption) at a constant temperature (25° C.) and 10% RH intervals over a 0-90% range (60 minutes for each humidity level). This type of experiment should demonstrate the ability of samples studied to absorb moisture (or not) over a set of well-determined humidity ranges.

Example 1—Preparation and Evaluation of Salts of RPL554

Solutions containing either 1 or 4 equivalents of the counter ion as set out in Table 1 were charged to agitated 23.4 ml solutions of RPL554 in dichloromethane (DCM) at a concentration of 17.1 mg/ml and at a temperature of 40° C. and allowed to cool to ambient temperature. The composition of the counter ion solutions are shown in Table 2.

TABLE 1

| Acid counter ions | Equivalents |
|---|---|
| Hydrochloric, aqueous | 4 |
| Sulfuric | 1 |
| Phosphoric | 1 |
| Hydrobromic | 4 |
| Naphthalene-1,5-disulfonic | 4 |
| Ethane-1,2-disulfonic | 1 |
| Ethane sulfonic | 1 |
| p-Toluene sulfonic | 4 |
| Methane sulfonic | 4 |
| Benzene sulfonic | 4 |
| 2-Naphthalene sulfonic | 1 and 4 |
| Hydrochloric, anhydrous | 4 |
| 1-Hydroxy-2-naphthoic | 1 and 4 |
| Pyromellitic | 1 and 4 |

TABLE 2

| Acids | Solvent | Conc., M | Volume used, µL for 1 equivalent | Volume used, µL for 4 equivalents |
|---|---|---|---|---|
| Hydrochloric acid | Ethanol | 2 | 12.5 | 50 |
| Sulfuric acid | Ethanol | 2 | 12.5 | 50 |
| Phosphoric acid | Ethanol | 2 | 12.5 | 50 |
| Hydrobromic acid | Ethanol | 2 | 12.5 | 50 |
| Naphthalene-1,5-disulfonic acid | THF | 1 | 25 | 100 |
| Ethane-1,2-disulfonic acid | Ethanol | 2 | 12.5 | 50 |
| Ethane sulfonic acid | THF | 2 | 12.5 | 50 |
| p-Toluene sulfonic acid | Ethanol | 2 | 12.5 | 50 |
| Methane sulfonic acid | THF | 2 | 12.5 | 50 |
| Benzene sulfonic acid | Ethanol | 2 | 12.5 | 50 |
| 2-Naphthalene sulfonic acid | THF | 1 | 25 | 100 |

Solids were observed to form with phosphoric, naphthalene-1,5-disulfonic and ethane-1,2-disulfonic acids. The volume of the reaction solvent was reduced by nitrogen stream to ca 2-5 ml. Tert-butylmetyl ether (TBME), 8 ml, was then charged to the mixtures affording precipitates and gummy solids which were agitated overnight. This afforded suspensions in some cases as well as returning gummy solids and mixtures which were further manipulated with DCM and TBME via trituration to afford suspensions. The mixtures were agitated for a further 4 hours prior to the isolation of the solids by filtration which were then dried in vacuo at 45° C.

The chemical purities of the isolated solids were determined by HPLC and are detailed in Table 3. The solids isolated with sulfuric, ethane sulfonic, methane sulfonic, 1-hydroxy-2-naphthoic, pyromellitic and hydrochloric (anhydrous) acids had slightly reduced chemical purities. There was no significant degradation of RPL554 with the counter ions and procedures employed.

TABLE 3

| Acid counter ions | Equivs. | Solid colour | Chemical purity, area % | Filtrate colour | $^1$H NMR Shift in resonances of RPL554 | $^1$H NMR API to counter ion Stoichiometry |
|---|---|---|---|---|---|---|
| Sulfuric | 1 | Off white | 95.15 | Colourless | Yes, salt | N/A |
| Phosphoric | 1 | Very pale yellow | 98.43 | Yellow | No | N/A |
| Hydrochloric, aqueous | 4 | White | 98.56 | Tan | Yes, salt | N/A |
| Ethane sulfonic | 1 | White | 97.94 | Tan | Yes, salt | 1:1 |
| Hydrobromic | 4 | White | 98.15 | Orange | Yes, salt | N/A |
| Methane sulfonic | 4 | White | 97.92 | Colourless | Yes, salt | 1:2 |
| Naphthalene-1,5-disulfonic | 4 | White | 99.08 | Amber | Yes, salt | 1:1 |
| Ethane-1,2-disulfonic | 1 | White | 98.09 | Tan | Yes, salt | 1:1 (approx) |
| p-Toluene sulfonic | 4 | White | 98.37 | Colourless | Yes, salt | 1:2 |
| Benzene sulfonic | 4 | Pale yellow | 98.06 | Colourless | Yes, salt | 1:2 |
| Hydrochloric, anhydrous | 4 | Very pale yellow | 96.62 | Colourless | Yes, salt | N/A |
| 2-Naphthalene sulfonic | 1 | White | 98.99 | Pale yellow | Yes, salt | 1:1 |
| 2-Naphthalene sulfonic | 4 | Off white | 98.31 | Colourless | Yes, salt | 1:2 |
| 1-Hydroxy-2-naphthoic | 1 | Yellow | | | No | 1:0.5 |
| 1-Hydroxy-2-naphthoic | 4 | Yellow | | | Slight shift | 1:1.35 |
| Pyromellitic | 1 | Pale yellow | 96.32 | | Slight shift | 1:0.92 |
| Pyromellitic | 4 | Pale yellow | 95.81 | | Slight shift | 1:1.47 |

$^1$H NMR spectra of the solids revealed shifts in the resonances of RPL554 consistent with salt formation except for phosphoric, 1-hydroxy-2-naphthoic and pyromellitic acids. The stoichiometry of the salts derived from sulfonic acid counter ions was found to be either 1:1 or 1:2, RPL554 to counter ion. For 1-hydroxy-2-naphthoic and pyromellitic acids the stoichiometries varied and salt formation was not definitive.

Figure 2:
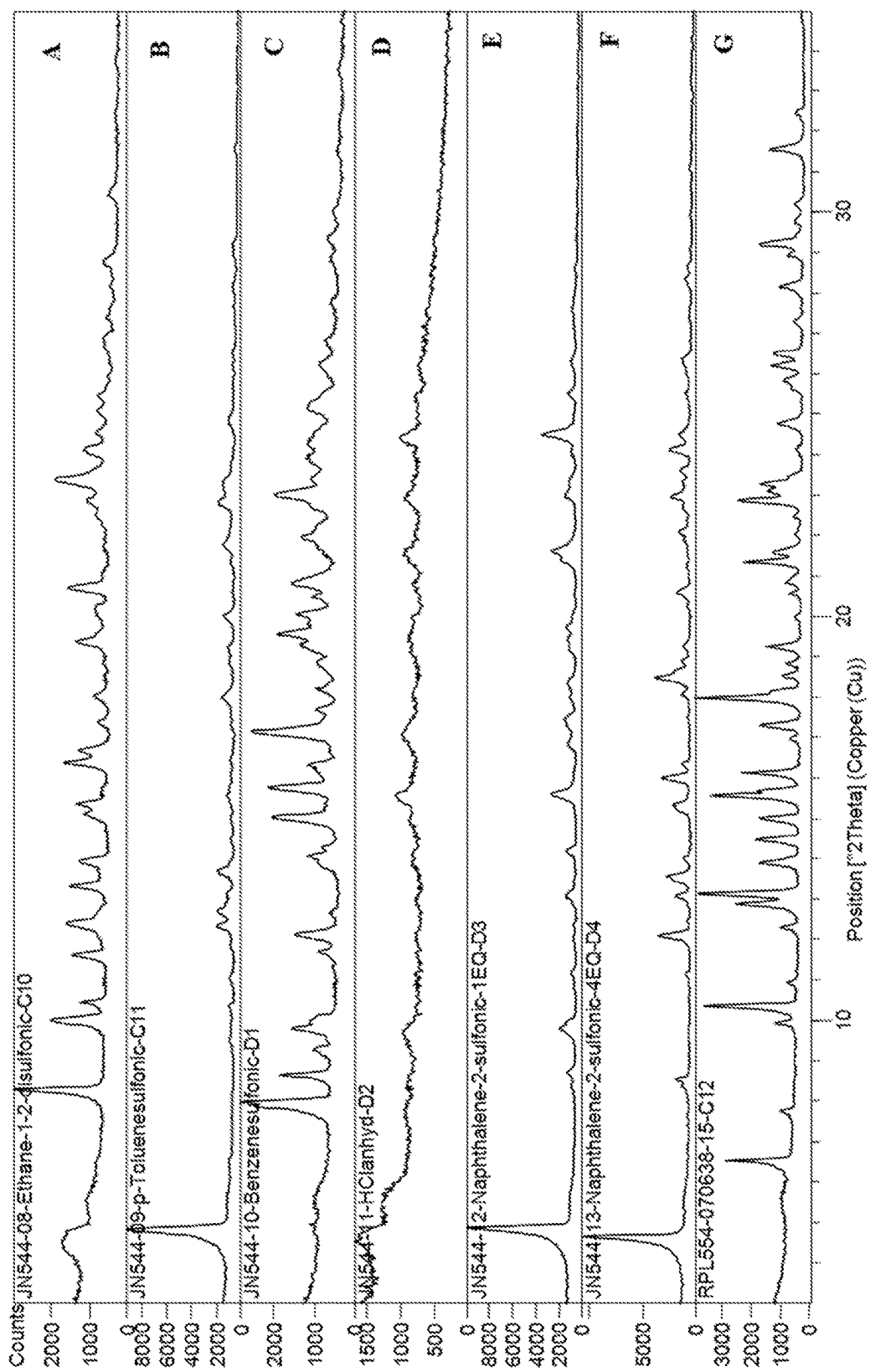
FIG. 2 shows XRPD patterns of solids isolated from RPL554 salt formation wherein the acid used is: ethane-1,2-disulfonic (A), p-toluenesulfonic (B), benzenesulfonic (C), hydrochloric-anhydrous (D), 2-naphthalenesulfonic-1 equivalent (E) and 2-naphthalenesulfonic-4 equivalents (F). The XRPD pattern of the RPL554 free base is also shown (G).
Figure 3:
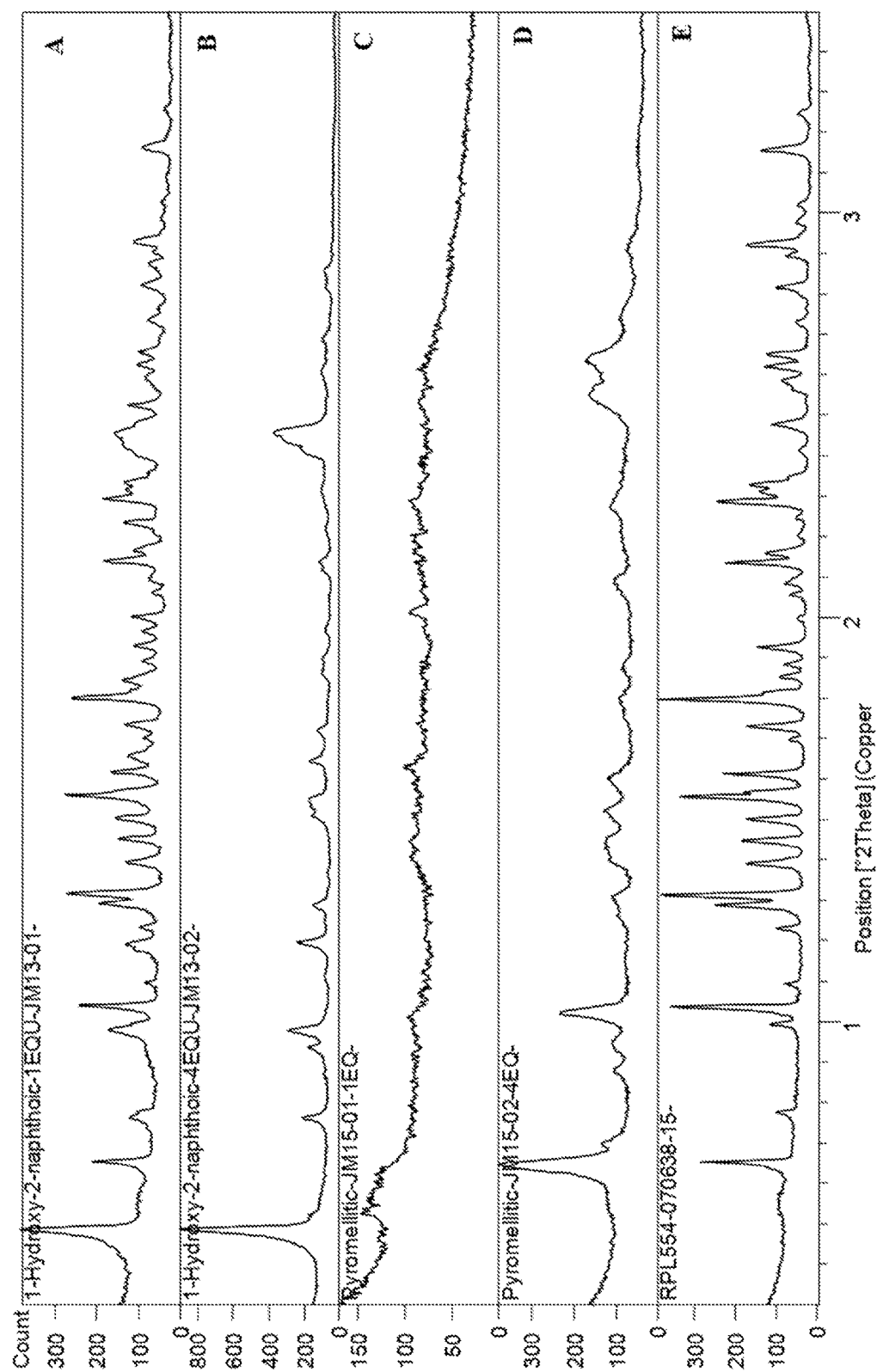
FIG. 3 shows XRPD patterns of solids isolated from RPL554 salt formation wherein the acid used is: 1-hydroxy-2-naphthoic-1 equivalent (A), 1-hydroxy-2-naphthoic-4 equivalents (B), pyromellitic-1 equivalent (C) and pyromellitic-4 equivalents (D). The XRPD pattern of the RPL554 free base is also shown (H).

The XRPD patterns (FIG. 1, FIG. 2 and FIG. 3) of the isolated solids revealed that modified versions of RPL554 had been generated with the appropriate acid counter ion equivalents and were of varying crystallinity and did not resemble RPL554 free base except for the solid isolated from 1-hydroxy-2-naphthoic acid, 1 equivalent. The XRPD pattern of the solid isolated from 1-hydroxy-2-naphthoic acid, 1 equivalent, contained reflections common to RPL554 together with additional reflections and indicated that this solid might perhaps be a solid mixture of RPL554 and 1-hydroxy-2-naphthoic acid. The XRPD patterns obtained are detailed in Table 4. Crystalline XRPD patterns were observed for most salts.

TABLE 4

| Acid counter ion | Stoichiometry, RPL554 to counter ion | Form |
|---|---|---|
| Sulfuric | not determined | Crystalline |
| Phosphoric | not determined | Crystalline |
| Hydrochloric, aqueous | not determined | Crystalline |
| Ethane sulfonic | 1:1 | Crystalline |

TABLE 4-continued

| Acid counter ion | Stoichiometry, RPL554 to counter ion | Form |
|---|---|---|
| Hydrobromic | not determined | Crystalline |
| Methane sulfonic | 1:2 | Crystalline |
| Naphthalene-1,5-disulfonic | 1:1 | Weakly crystalline |
| Ethane-1,2-disulfonic | 1:1 (approx) | Crystalline |
| p-Toluene sulfonic | 1:2 | Crystalline |
| Benzene sulfonic | 1:2 | Crystalline |
| Hydrochloric, anhydrous | not determined | Very weakly crystalline |
| 2-Naphthalene sulfonic, 1 equivalent | 1:1 | Crystalline |
| 2-Naphthalene sulfonic, 4 equivalents | 1:2 | Crystalline |
| 1-Hydroxy-2-naphthoic, 1 equivalent | 1:0.5 | Crystalline - possible mixture |
| 1-Hydroxy-2-naphthoic, 4 equivalents | 1:1.35 | Crystalline |

TABLE 4-continued

| Acid counter ion | Stoichiometry, RPL554 to counter ion | Form |
|---|---|---|
| Pyromellitic, 1 equivalent | 1:0.92 | Very weakly crystalline |
| Pyromellitic, 4 equivalents | 1:1.47 | Crystalline |

The physico-chemical characteristics of the salt candidates were determined. These are given in Table 5.

TABLE 5

| Counter ion | CP of RPL554 by HPLC, area % | Stoichiometry, API: Counter ion by NMR or IC | Form of solid XRPD/NMR | DSC, °C. | TGA, weight reduction, % | Solubility as RPL554 in water, mg/ml | pH of aqueous suspension/ solution | Form of solid post water maturation |
|---|---|---|---|---|---|---|---|---|
| Sulfuric - ethanol solution | 98.82 | ND Ethanol solvate, stoichiometric | Crystalline Salt formation | Endo broad, 130 - Form change? Endo, 193.5, melt | 2.37% up to ca 85° C. - loss of water | 2.52 | 3.28 Suspension | No change |
| Sulfuric - ethanol solution Repeat | ND | ND[1] Ethanol solvate, stoichiometric | Crystalline Salt formation | ND | NR | ND | ND | ND |
| Sulfuric - aqueous solution | ND | 1:≈1 (0.84) | Crystalline Salt formation | Endo broad, 122 - Form change? Endo, 185 - Form change/ melt? Endo, 264 - melt? | 0.53% up to ca 55° C. - loss of water 3.45% coincident with endo at 185° C. - de-hydration | 12.17 | 1.87 Suspension | No change |
| Phosphoric | 99.35 | ND | Crystalline Salt formation assumed | Endo, 148.9, melt | 2.83% coincident with endo | >22.52 | 3.08 Solution | Not known No solid recovered |
| Phosphoric Repeat | ND | 1:≈1 (0.77) | Crystalline Salt formation assumed | Endo, 145.8, melt | NR | ND | ND | ND |
| Hydrochloric aqueous source | 98.48 | ND | Crystalline Salt formation | Endo, 156.6, melt | 4.17% to ca 125° C. - loss of water | 4.95 | 3.84 Suspension | No change |
| Hydrochloric aqueous source Repeat | ND | 1:≈1 (0.90) | Crystalline Salt formation | Endo, 156.8, melt | NR | ND | ND | ND |
| Ethane sulfonic | 98.79 | 1:1 | Crystalline Salt formation | Endo broad, 108.9 - Form change? Endo, 219.2, melt | 1.54% up to ca 50° C. - loss of water | >21.69 | 3.04 Solution | Not known No solid recovered |
| Ethane sulfonic Repeat | ND | 1:1 | Crystalline Salt formation | Endo broad, 86.4 - Form change? Endo, 219.6, melt | NR | ND | ND | ND |
| HBr | 97.90 | ND | Crystalline Salt formation | Endo, 174.1, melt | 3.74% to ca 135° C. - loss of water | 3.66 | 3.20 Suspension | No change |
| Methane sulfonic | 97.37 | 1:1 | Crystalline Salt formation | Endo, 219.7, melt | 0.5% up to ca 65° C. - loss of water | 21.15 | 2.69 Solution | Not known No solid recovered |
| Naphthalene-1,5-disulfonic | 99.29 | 1:0.5 | Crystalline Salt formation | Endo, 266.2, melt | 2.12% up to ca 110° C. - loss of water | 0.00 | 3.37 Suspension | No change |
| Ethane-1,2-disulfonic | 98.91 | 1:0.5 | Crystalline Salt formation | Endo, 216.8, melt | 1.95% up to ca 120° C. - loss of water | 1.89 | 3.72 Suspension | No change |
| p-Toluene sulfonic | 96.86 | 1:1 | Crystalline Salt formation | Endo, 207.5, melt | 1.28% up to ca 85° C. - loss of water | 0.70 | 3.40 Suspension | No change |
| Benzene sulfonic | 97.61 | 1:1 | Crystalline Salt formation | Endo, 161.6, melt | 2.43% up to ca 140° C. - loss of water | 1.47 | 3.43 Suspension | No change |
| Hydrochloric anhydrous source | 96.98 | ND | Crystalline Salt formation | Endo, 154.7, melt | 3.43% to ca 120° C. - loss of water | 5.16 | 3.68 Suspension | No change |
| Naphthalene-2-sulfonic | 95.88 | 1:1 | Crystalline Salt formation | Endo, 232.5, melt | Weight reduction post endo | 0.09 | 4.74 Suspension | No change |

TABLE 5-continued

| Counter ion | CP of RPL554 by HPLC, area % | Stoichiometry, API: Counter ion by NMR or IC | Form of solid XRPD/NMR | DSC, °C. | TGA, weight reduction, % | Solubility as RPL554 in water, mg/ml | pH of aqueous suspension/ solution | Form of solid post water maturation |
|---|---|---|---|---|---|---|---|---|
| 1-Hydroxy-2-naphthoic | 97.80 | 1:≈1.1 | Poorly crystalline No salt formation | Two endos, 166.5 and 180.6 - mixture of species | NR | 0.01 | 3.71 Suspension | No change |
| Pyromellitic | 97.49 | 1:≈1.25 | Poorly crystalline Salt formation | Two endos, 162.7 and 199.2 - mixture of species | NR | 0.17 | 2.27 Suspension | Slight change |

ND—not determined,
NR—not recorded

Example 2—Solubility of RPL554 Salts in Saline Solutions, Water and Aqueous Buffer Solutions at 25° C.

The behaviour of salts of RPL554 were examined under the following conditions:

Phosphate buffered to pH 3.5 in saline, 0.9% w/w at 25° C.

Acetate buffered to pH 4.5 in saline, 0.9% w/w at 25° C.

Citro-Phosphate buffered to pH 4.5 in saline, 0.9% w/w at 25° C.

Phosphate buffered to pH 6.5 in saline, 0.9% w/w at 25° C.

Saline, 0.7, 0.9 and 1.1% w/w at 25° C.

Deionised water at 25° C.

RPL554 salts and RPL554, ca 50 mg, were suspended in the various aqueous media, 1 ml, with agitation at the specified temperatures for 24 hours. The solids were isolated and dried in vacuo at 45° C. The retained filtrates were examined by HPLC.

Additional RPL554 methane sulfonate salt, ca 50 mg, was charged to the water mixtures at 25° C. and 37.5° C. in order to afford a suspension. In all other cases, suspensions were obtained.

The solubility of the RPL554 was determined by HPLC using a single point calibration and is expressed as RPL554 and not as the salt and are detailed in Table 6 and Table 7 for the various conditions utilised.

TABLE 6

Solubility as RPL554 (mg/ml) in saline and water at 25° C.

| Counter ion | 0.7 w/w % Saline | 0.9 w/w % Saline | 1.1 w/w % Saline | Water |
|---|---|---|---|---|
| Phosphate | 7.22 | 4.78 | 2.86 | 41.84 |
| Methane sulfonate | 5.01 | 3.73 | 2.52 | 44.52 |
| Ethane-1,2-disulfonate | 4.79 | 4.12 | 1.03 | 3.69 |
| Hydrochloride | 2.85 | 1.93 | 2.48 | 12.66 |
| Sulfate | 2.78 | 1.94 | 1.35 | 12.11 |
| Benzenesulfonate | 2.27 | 2.74 | 2.94 | 2.57 |
| Ethanesulfonate | 1.62 | 0.79 | 1.27 | 21.37 |
| Hydrobromide | 0.95 | 0.82 | 0.66 | 3.43 |
| p-Toluenesulfonate | 0.83 | 0.62 | 0.8 | 1.01 |
| Naphthalene-2-sulfonate | 0.17 | 0.09 | 0.09 | 0.13 |
| Naphthalene-1,5-disulfonate | 0.01 | 0 | 0.01 | 0.01 |
| None (RPL554) | 0 | 0 | 0 | 0 |

TABLE 7

Solubility as RPL554 (mg/ml) in buffer solution at 25° C.

| Counter ion | pH 3.5, Phosphate | pH 4.5, Acetate | pH 4.5, Citro-phosphate, | pH 6.5, Phosphate |
|---|---|---|---|---|
| Ethane-1,2-disulfonate | 2.66 | 1.47 | 4.14 | — |
| Phosphate | 1.84 | 1.67 | 3.29 | 0.02 |
| Methanesulfonate | 1.72 | 2.01 | 3.10 | 0.02 |
| Hydrochloride | 1.07 | 1.38 | 1.93 | 0.02 |
| Sulfate | 1.22 | 0.42 | 1.75 | 0.00 |
| Benzenesulfonate | 1.10 | 1.39 | 1.57 | 0.00 |
| Ethanesulfonate | 1.18 | 0.46 | 1.55 | 0.00 |
| Hydrobromide | 0.33 | 0.71 | 0.75 | 0.00 |
| p-Toluenesulfonate | 0.18 | 0.77 | 0.61 | 0.00 |
| Naphthalene-2-sulfonate | 0.08 | 0.41 | 0.28 | 0.00 |
| None (RPL554) | 0.30 | 0.24 | 0.22 | 0.00 |
| Naphthalene-1,5-disulfonate | 0.00 | 0.01 | 0.00 | 0.00 |

It has been shown that ethane-1,2-disulfonate, phosphate, methanesulfonate, hydrochloride, sulfate, benzenesulfonate and ethanesulfonate salts of RPL554 have particularly favourable solubility characteristics. In particular, the solubility in a pH 4.5 citro-phosphate buffer allows the production of higher concentration formulations with reduced acidity as compared with other salt solutions.

Example 3—Thermal Manipulation and Behaviour to Humidity

The nature of the hydration and a preliminary examination of salt robustness/polymorphism was assessed by thermal manipulation using ThermoGravimetric Analysis (TGA) and Gravimetric Vapor Sorption (GVS).

RPL554 hydrochloride showed reversible water uptake under ambient conditions with no change in form and is likely to be a stable version of the salt. No form change was detected by thermal manipulation of the salt below the melt endotherm.

Figure 4:
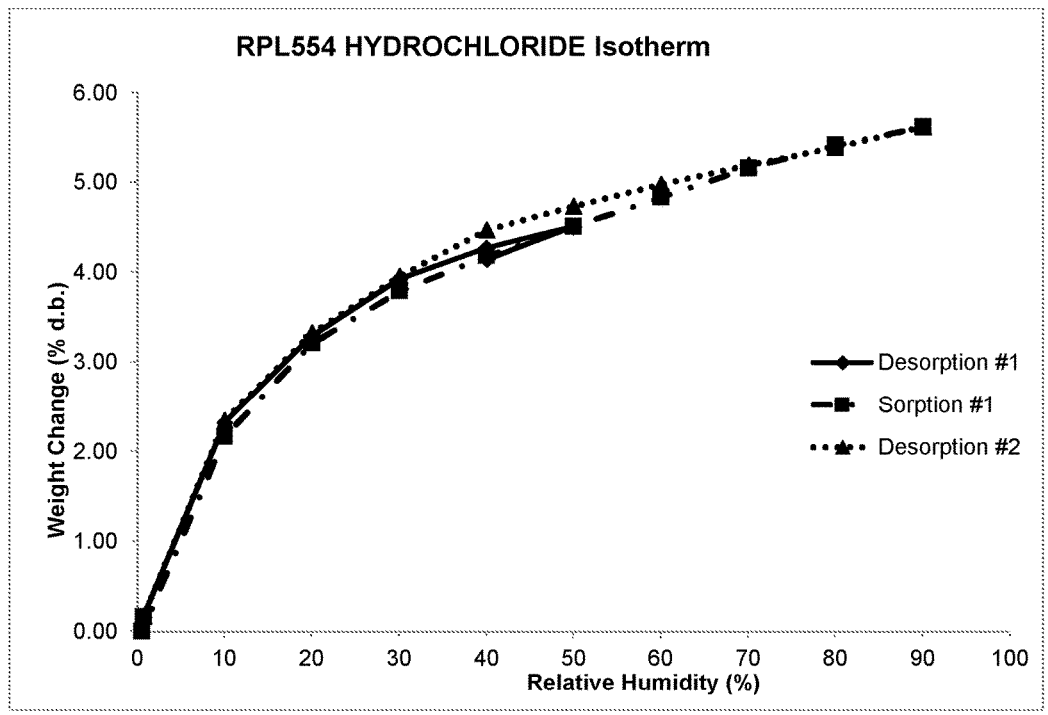
FIG. 4 shows the gravimetric vapour sorption (GVS) profile of RPL554 hydrochloride.
Figure 5:
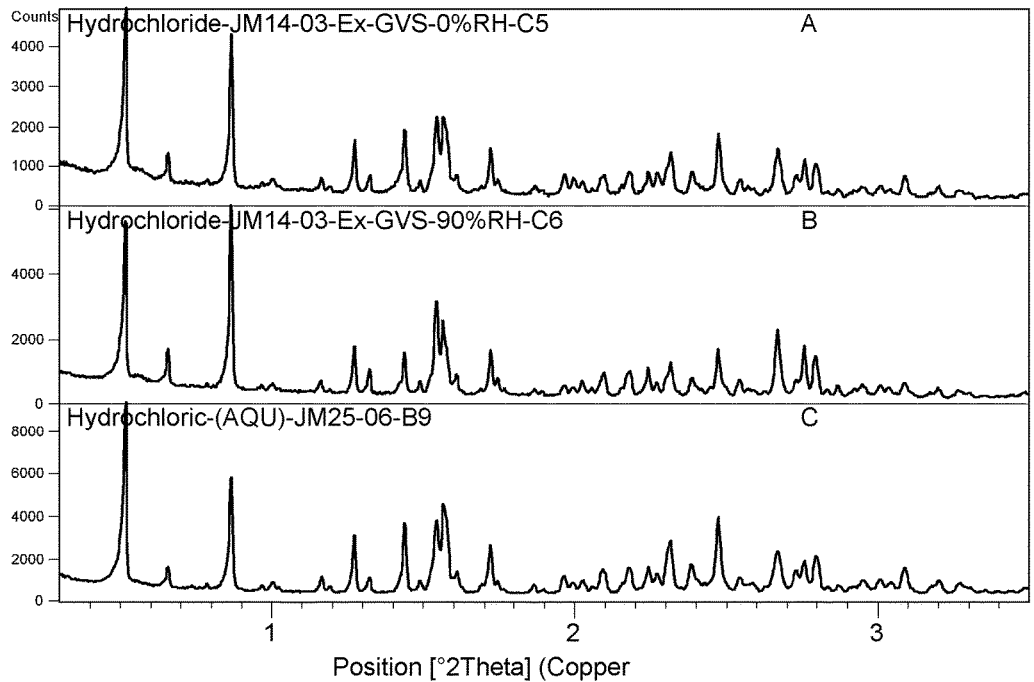
FIG. 5 shows XRPD patterns of RPL554 hydrochloride for 0% humidity (A), 90% humidity (B) and as initially input (C).

The behaviour of the hydrochloride salt to humidity was studied by GVS over desorption, sorption and desorption cycles as illustrated in FIG. 4. The hydrochloride salt displayed reversible adsorption and desorption over the humidity range with no hysteresis. The salt was an anhydrate at 0% humidity and reversibly adsorbs water (up to 2 mole equivalents), up to 90% humidity. The XRPD patterns of RPL554 hydrochloride for 0% humidity (A), 90% humidity (B) and input form (C) are shown in FIG. 5, and demonstrated form stability over the humidity range, and reversible wetting/hydration.

Figure 6:
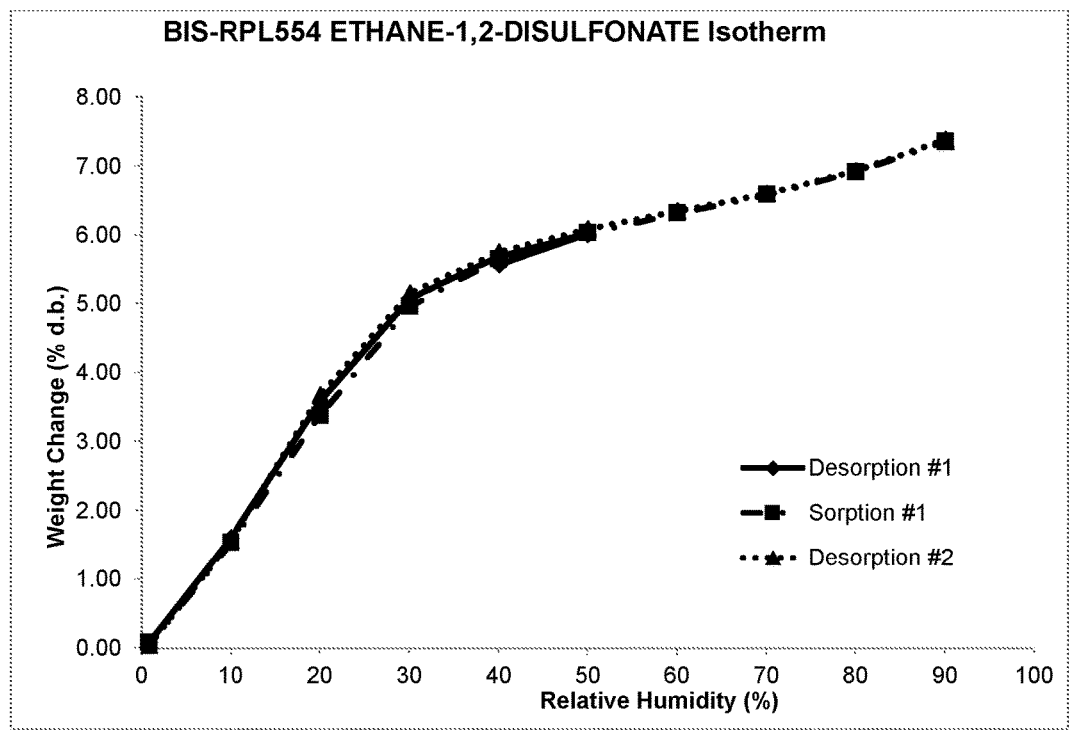
FIG. 6 shows the GVS profile of bis-RPL554 ethane-1,2-disulfonate.

The behaviour of the bis-RPL554 ethane-1,2-disulfonate to humidity by GVS over desorption, sorption and desorption cycles as illustrated in FIG. 6. The ethane-1,2-disulfonate salt displayed reversible adsorption and desorption over the humidity range with no hysteresis. The salt was an anhydrate at 0% humidity and adsorbs water (up to 5 mole equivalents), up to 90% humidity. The water uptake to 50% humidity equated to 4 mole equivalents, which then converted to 5 mole equivalents at 90% humidity.

Figure 7:
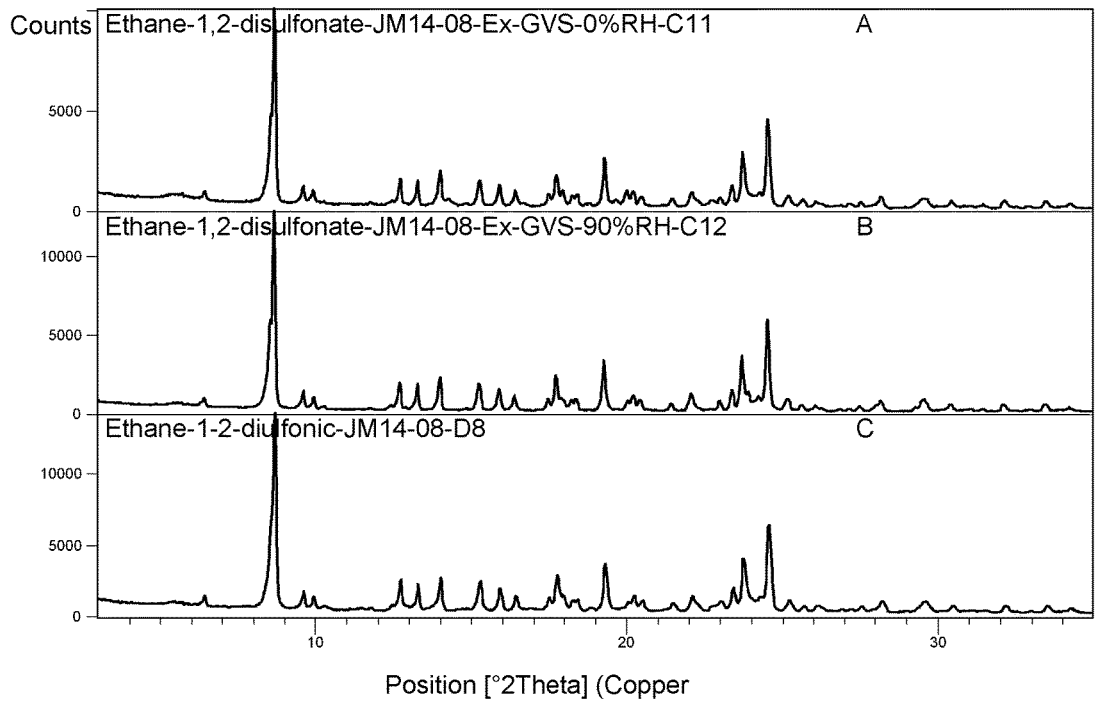
FIG. 7 shows XRPD patterns of bis-RPL554 ethane-1,2-disulfonate for 0% humidity (A), 90% humidity (B) and as initially input (C).

The XRPD patterns, FIG. 7, of the bis-RPL554 ethane-1,2-disulfonate salt at 0 and 90% humidity were the same as the input form of the salt and demonstrated form stability over the humidity range and reversible wetting/hydration.

A summary of the results of the thermal and humidity tests is given in Table 7.

TABLE 7

| Counter ion | Isothermal 105° C., 2 hours | Thermal cycle | Behaviour to humidity | Comment |
| --- | --- | --- | --- | --- |
| Hydrosulfate | No form change or significant weight reduction. | Form change by XRPD Endotherms at 122 and 185° C. are removed. New endotherm at 219° C. | Tetrahydrate above 30% humidity and an anhydrate at 0% humidity. Hysteresis between 0 and 30% humidity and reversible. Form change for anhydrate and tetrahydrate. | Disparity between isothermal and thermal cycle data - different form behaviour. Thermal and humidity induced form changes dependent upon the conditions with no cross correlation. Tetrahydrate form stable above 30% humidity. |
| Phosphate | Form change - similar to RPL554 by XRPD but not DSC - (possible degradation) | Form change - similar to RPL554 by XRPD but not DSC - (possible degradation) | Reversible adsorption and desorption over the humidity range with no hysteresis. No salt hydration, except for wetting. Form stability at extremes of humidity. | New thermal characteristic exotherm and endotherm coincident with weight loss by TGA. Satisfactory behaviour to variable humidity with no form change. |
| Hydrochloride | Reversible water uptake. No form change. | Stable form | Anhydrate at 0% humidity and dihydrate, up to 90% humidity with reversibility. No hysteresis. Form stability at extremes of humidity. | Reversible water uptake, no form change under thermal or humidity conditions. Reversible hydration of the salt. |
| Ethane sulfonate | No variable water uptake. No form change. | No form change by XRPD. Endotherm at 86° C. removed. No change in main endotherm. | Monohydrate above 40% humidity and an anhydrate at 0% humidity. Hysteresis between 0 and 40% humidity and reversible. Form change for anhydrate and mono-hydrate. | Disparity between isothermal and thermal cycle data - different form behaviour. Monohydrate form stable above 40% humidity. |
| Methane sulfonate | No variable water uptake. No form change. | Not conducted | Reversible adsorption and desorption over the humidity range. Hysteresis between 30 and 70% humidity. Adsorption - di-hydrate at 70% humidity and tetra-hydrate at 90% humidity. Desorption - di-hydrate at 70% humidity and mono-hydrate at 40% humidity, converting to anhydrate at 0% humidity. Form change for an-hydrate and tetra-hydrate | No variable water uptake or form change under thermal conditions. Hysteresis between 30 and 70% humidity and variable hydration. |
| Ethane-1,2-disulfonate | No form change. | Not conducted | Reversible adsorption and desorption over the humidity range with no hysteresis. Anhydrate at 0% humidity to tetrahydrate at 50% humidity and up to, pentahydrate at 90% humidity. Form stability and reversible hydration at extremes of humidity | No evidence of form change. Reversible adsorption and desorption over the humidity range with no hysteresis. 'Loose' non-formal hydration of the salt. |
| Benzene sulfonate | No form change. | Not conducted | Not conducted | No evidence of form change. |

Conclusion

On the basis of the above investigations into the solubility and stability of various salts of RPL554 it has been found that ethane-1,2-disulfonate, phosphate, methanesulfonate, hydrochloride, sulfate, benzenesulfonate, ethanesulfonate, hydrobromide and p-toluenesulfonate are the preferred salts of RPL554. The ethane-1,2-disulfonate, phosphate, methanesulfonate, hydrochloride, sulfate, benzenesulfonate and ethanesulfonate salts are particularly preferred. The ethane-1,2-disulfonate and hydrochloride salts have been found to have the most preferred properties on the basis of solubility and thermal stability at different humidities.

Further Development

Example 4—Formation and Characterisation of RPL554 Salts

RPL554 Salt Formations

Salt formations were carried out in three sets of three with the acids chosen, the solvent they were dissolved in to 2M concentration and the equivalents added to 7 g of the base in DCM shown in Table 8 (which sets out the acids used during the salt formation with volume and mmol calculations based in the relevant equivalents of 2M acid being added to 7 g RPL554 in DCM).

TABLE 8

| Acid counter ion | Solvent for counter ion | Equivalents | Volume (ml) | Acid mmol |
|---|---|---|---|---|
| Hydrochloric | EtOH, 2M | 4 | 29.32 | 58.63 |
| Phosphoric | EtOH, 2M | 1 | 7.33 | 14.66 |
| Methanesulfonic | EtOH, 2M | 4 | 29.32 | 58.63 |
| Ethanesulfonic | THF, 2M | 1 | 7.33 | 14.66 |
| Ethane-1,2-disulfonic | EtOH, 2M | 1 | 7.33 | 14.66 |
| Sulfuric | EtOH, 2M | 1 | 7.33 | 14.66 |
| Benzenesulfonic | EtOH, 2M | 4 | 29.32 | 58.63 |
| p-Toluenesulfonic | EtOH, 2M | 4 | 29.32 | 58.63 |
| Hydrobromic | EtOH, 2M | 4 | 29.32 | 58.63 |

Series 1

6.995, 7.005 and 7.004 g RPL554 were weighed into the first three flasks, charged with 410 ml DCM (based on the solubility of the base in DCM being 17 mg/ml), heated to 40° C. and stirred for 1 hour before the planned addition of ethanesulfonic, ethane-1,2-disulfonic and sulfuric acid respectively. However, the base did not dissolve in the given volume of DCM. An additional 50 ml was added to each flask and stirred at temperature for 30 minutes, but dissolution did not occur until a further 50 ml of DCM was added and stirred, delivering a clear, yellow solution. The three acids were charged to the appropriate flasks, with a lightening in the colour of the clear solution observed with the ethanesulfonic and sulfuric acid whereas ethane-1,2-disulfonic acid created a white precipitate upon addition. The three solutions were left to stir to at ambient temperature overnight.

The clear, pale yellow solution of the ethanesulfonate was reduced to ca. 20 ml, producing a clear, yellow solution which crystallised to give a mobile solid. TBME (tert-butyl methyl ether, 30 ml) was added and the suspension was stirred for ca. 1½ hours before isolating with a 25 ml TBME cake rinse, leaving a pale yellow solid.

The white, thin slurry suspension of the ethane-1,2-disulfonate was reduced to ca. 100 ml to thicken the slurry before isolating with a 25 ml TBME cake rinse, leaving an off-white solid.

The clear, pale yellow solution of the sulphate was reduced to ca. 20 ml, producing a clear, dark yellow solution. The addition of TBME (50 ml) initially caused a gum to form but trituration and stirring for ca. 3 hours yielded crystallised solids which were isolated with 30 ml TBME cake rinse, leaving a pale yellow solid.

The three salts were dried in vacuo at 60° C. for ca. 40 hours.

Series 2

Following the initial attempts to dissolve the RPL554 in 6.5 vol DCM, 6.993, 7.001 and 7.003 g RPL554 were weighed into the second set of three flasks before being charged with 500 ml DCM and stirred to 40° C. for ca. 45 minutes to achieve dissolution before the addition of benzenesulfonic, p-toluenesulfonic and hydrobromic acid respectively, causing the three yellow solutions to pale in colour, before allowing to stir to ambient.

The clear, pale yellow solution of the benzenesulfonate was left to stir overnight before reducing to ca. 30 ml then gradually adding 125 ml TBME which resulted in a precipitate that was stirred for ca. 30 minutes before isolating with a 25 ml TBME cake rinse, leaving a pale yellow solid.

Both the p-toluenesulfonate and hydrobromide solutions were reduced to 30 ml before the addition of 125 ml TBME to each then leaving to stir overnight. The p-toluenesulfonate had developed a mildly gummy solid that was able to be crushed down then stirred for ca. 2½ hours before isolation with a 25 ml TBME rinse, leaving a pale yellow solid, whereas the hydrobromide had yielded a sticky gum that required trituration to develop a seedbed before stirring for ca. 4 hours then isolating with a 25 ml TBME rinse, delivering an off-white solid.

The three salts were dried in vacuo at 60° C. for ca. 16 hours then at 45° C. for ca. 60 hours.

Series 3

7.005, 6.993 and 6.997 g RPL554 were weighed into the final set of three flasks before charging with 500 ml DCM and stirring to dissolution at 40° C. after ca. 30 minutes before the addition of hydrochloric, phosphoric and methanesulfonic acid respectively, causing the three yellow solutions to pale in colour, and leaving to stir ambient overnight for ca. 16 hours. The solutions were reduced to ca. 30 ml before the gradual addition of 125 ml TBME.

Both the hydrochloride and mesylate solutions formed strong, mobile precipitates that were left to stir for one hour before isolating with a 25 ml TBME cake rinse, delivering off-white solids.

The phosphate solution initially produced a gum upon the addition of TBME however physically crushing the lumps and allowing to stir for ca. 2 hours yielded a uniform slurry. Isolating with a 25 ml TBME cake rinse delivered yellow solids along with a bright yellow filtrate. These solids, along with the hydrochloride and mesylate, were dried in vacuo at 45° C. for ca. 60 hours.

As the other filtrates so far obtained were either colourless or very pale, the phosphate filtrate was reduced, delivering yellow solids which were isolated by filtration and dried in vacuo at 60° C. for ca. 16 hours.

The results of the salt formation, regarding recovery and fate, are summarised in Table 9. The ethanesulfonate and two phosphate salts were not carried forward into water maturation, based on previous investigations, and so underwent full analysis. Initial analysis of the hydrochloride by XRPD suggested that water maturation would be unnecessary, however analysis by DSC revealed slightly different thermal properties to the previously obtained salt and so the hydrochloride underwent water maturation.

TABLE 9

| Salt Counter Ion | Mass (g) | Recovery (%)* | H₂O Matured |
| --- | --- | --- | --- |
| Hydrochloride | 6.339 | 84.07 | Yes |
| Phosphate | 4.812 | 87.56 | No |
| Phosphate | 2.567 |  | No |
| Mesylate | 12.774 | Quantitative | Yes |
| Ethanesulfonate | 8.588 | 99.77 | No |
| Ethane-1,2-disulfonate | 8.207 | 97.70 | Yes |
| Sulphate | 9.634 | Quantitative | Yes |
| Benzenesulfonate | 11.327 | Quantitative | Yes |
| p-Toluenesulfonate | 12.246 | Quantitative | Yes |
| Hydrobromide | 9.008 | Quantitative | Yes |

*The recovery is not indicative of active content, nor adjusted for solvents.

Water Maturation of the RPL554 Salts

All of the salts besides the hydrochloride, phosphate and ethanesulfonate were slurried in water (30-60 ml) for ca. 21-22 hours at 20° C. and the hydrochloride was slurried in water (30 ml) for 6 hours at 22° C. Variation in the volumes of water used is due to the volume of water required to deliver sufficiently mobile suspensions. Benzenesulfonate, p-toluenesulfonate and the hydrobromide initially formed gums but prolonged stirring delivered mobile suspensions (clear form/version change).

All water matured salts were isolated with a damp cake water rinse before drying in vacuo at 60° C. for ca. 19 hours. Details of the mass input, recovery and water volumes are given in

TABLE 10

Table 10

| Salt Counter Ion | Mass (g) Input | Mass (g) Out | Recovery (%) | Water added (ml) |
| --- | --- | --- | --- | --- |
| Hydrochloride | 5.89 | 5.01 | 85.06 | 30 |
| Mesylate | 11.77 | 5.19 | 44.10 | 50 |
| Ethane-1,2-disulfonate | 7.15 | 6.37 | 89.10 | 50 |
| Sulphate | 8.66 | 6.69 | 77.25 | 50 |
| Benzenesulfonate | 10.25 | 7.54 | 73.56 | 30 |
| p-Toluenesulfonate | 11.24 | 8.24 | 73.31 | 60 |
| Hydrobromide | 8.01 | 6.24 | 77.90 | 60 |

The water matured salts generally all delivered either more crystalline material by XRPD than the input salt or delivered a salt that matches existing patterns, apart from the HCl salt which remained unchanged (as anticipated by XRPD, intended to improve thermals).

Because of this, a small sample (52.1 mg) of the hydrochloride salt was subject to a second extended water slurry (0.2 ml) for ca. 21 hours at 22° C. before isolation with a damp cake water rinse. The sample was dried in vacuo at 60° C. for ca. 18 hours, yielding 37.2 mg (71.40% recovery) of salt. Analysis by XRPD, DSC and TGA however revealed little difference to the input material and so extended water maturation of the rest of the RPL554.HCl salt was deemed unnecessary.

Example 5—Milling of RPL554 Salts

Tests were carried out to identify whether the RPL554 salt forms according to the invention can be milled satisfactorily. Scanning Electron Microscopy (SEM) and visible light microscopy were performed on the APIs pre- and post-micronisation.

The jet milling activity was performed using a single pass milling operation, at an experimentally dictated grinding pressure. Only material recovered from the micronised product outlet was retained; i.e. material that has coated the inside of the jet mill was not recovered. Qualitative assessment of the ease of micronisation was noted.

Jet-Milling Performance

Eight of the salts produced in Example 4 were milled. These salts were the ethanesulfonate salt, the p-toluenesulfonate salt, the mesylate (methanesulfonate) salt, the benzenesulfonate salt, the sulfate salt, the hydrochloride salt, the ethane-1,2-disulfonate hemi-salt and the hydrobromide salt.

All eight batches of sample salts were successfully jet milled with a Sturtevant jet-mill. All eight batches were processed with the following parameters: a grinding pressure of 60 PSI and a venture pressure of 80 PSI.

Before jet-milling, a pestle and mortar were used to lightly grind all sample powders, with the exception of the ethanesulfonate salt. This process step was incorporated to break down large aggregates that existed in a number of the sample batches. However, for the ethanesulfonate salt, the grinding was not necessary because the large aggregates could be easily broken down with the spatula.

Some differences in the milling behaviour of the sample powders was observed. In general, seven salts behaved similarly when jet-milled, with yields ranging from approximately 45% to 70% as shown in Table 11. It was observed that the ethanesulfonate, hydrochloride and hydrobromide salt were most readily milled compared to the other salts. In addition, all eight salts demonstrated a degree of cohesive behaviour before and after milling.

All the sample batches were subjected to SEM analysis pre- and post-jet-milling. The SEM analysis illustrated comparable qualitative particle sizes post jet milling for all materials. It is estimated that the particle size ranges approximately between 1 and 3 µm.

TABLE 11

| Sample Salts | Input (g) | Output (g) | Yield (%) | Milling Time (min) | Ease of Milling |
| --- | --- | --- | --- | --- | --- |
| ethanesulfonate salt | 3.89 | 2.75 | 70.7 | 5.0 | Easy |
| p-toluenesulfonate salt | 7.80 | 4.26 | 54.6 | 12.0 | Intermediate |
| mesylate salt | 4.94 | 2.22 | 44.9 | 9.5 | Intermediate |
| benzenesulfonate salt | 7.22 | 4.20 | 58.2 | 7.0 | Intermediate |
| sulfate salt | 6.21 | 1.31 | 21.1 | 15.0 | Hard |
| hydrochloride salt | 4.56 | 2.60 | 57.0 | 6.0 | Easy |
| ethane-1,2-disulfonate hemi-salt | 6.12 | 2.74 | 44.8 | 13.2 | Intermediate |
| hydrobromide salt | 5.82 | 3.01 | 51.8 | 5.3 | Easy |

Example 6—Characterisation of Micronised Salts

The micronised salts were characterised by XRPD, DSC and TGA analysis. The majority of the salts were essentially unchanged by micronisation, other than the expected particle size reduction, which led to fine particles in all salts as observed by microscopy.

$^1$H NMR analysis of the micronised salts reveals no composition variance and generally reduced levels of residual solvent compared to the non-micronised salts.

Some differences in DSC profiles were observed with some salts. The methanesulfonate (mesylate), ethanesulfonate (esylate) and sulfate salts all showed broad endotherms around 100° C. that were not fully correlated to percentage weight loss in the TGA and may suggest some kind of thermal modification.

The TGA profiles generally exhibited endotherm-corresponding mass losses, although there was some variation in the amount of initial mass loss from 30° C. in all salts except for the hydrochloride and mesylate.

Example 7—Measurement of Intrinsic Dissolution Rate

The intrinsic dissolution rates of eight salts of RPL554 were measured to determine which salts had the most favourable dissolution properties.

Dissolution Study

The dissolution assay (pH-dependent sample dissolution) was investigated using the Sirius inForm.

Dissolution of a compressed tablet of the compound was monitored in a pH 7.0 aqueous dissolution experiment (0.15 M NaCl) at 37° C. using UV-absorption spectroscopy in 2 hour experiments. A tablet with a diameter of 3 mm, requiring approximate weights of 10 mg was compressed under a weight of 100 kg load force. Only one face of the tablet was exposed to the dissolution medium, which contained a 0.01 M acetate/phosphate buffer system to minimise perturbation of the experimental pH from dissolution of the drug.

Once the pH was adjusted to 7.0, the tablet disk was automatically lowered into the 40 mL aqueous media, allowing instantaneous data collection as soon as the sample was introduced. Stirring of the solution was continuous and at a constant rate of 100 rpm. The absorption data was converted to absolute sample weights using previously determined, pH-dependent, molar extinction coefficients. An appropriate wavelength range was chosen to ensure that spectroscopic data with an absorption value of <1.3 was analysed, avoiding erroneous dissolution results due to saturation of the UV light source.

Figure 8:
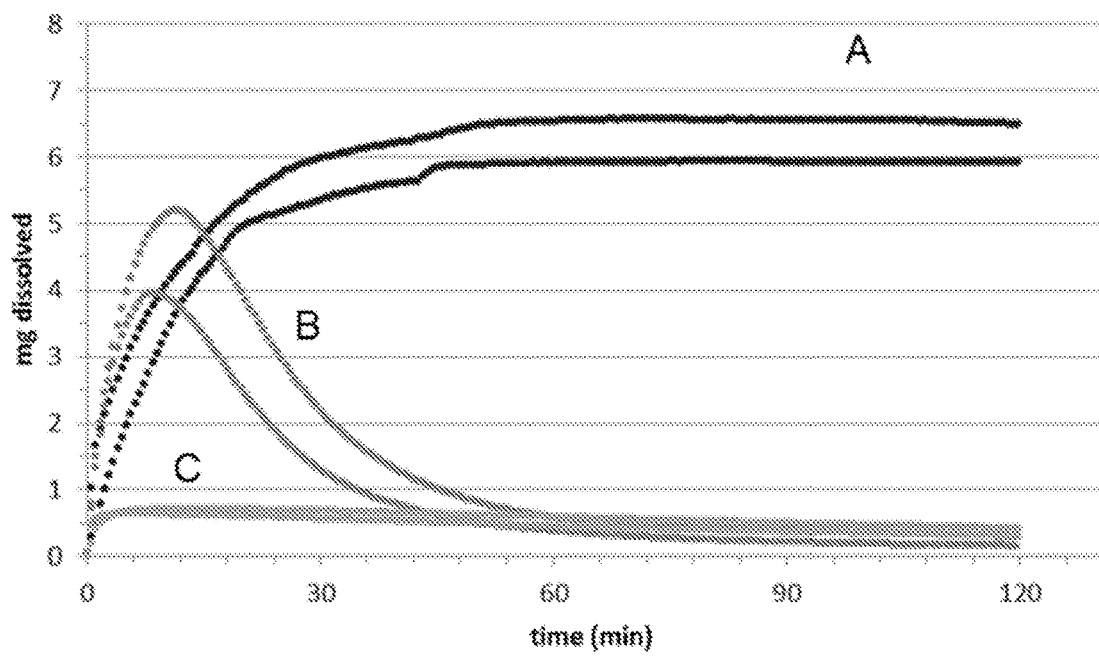
FIG. 8 shows the intrinsic dissolution of the sulfate (A), methanesulfonate (B) and ethanesulfonate (C) salts of RPL554.
Figure 9:
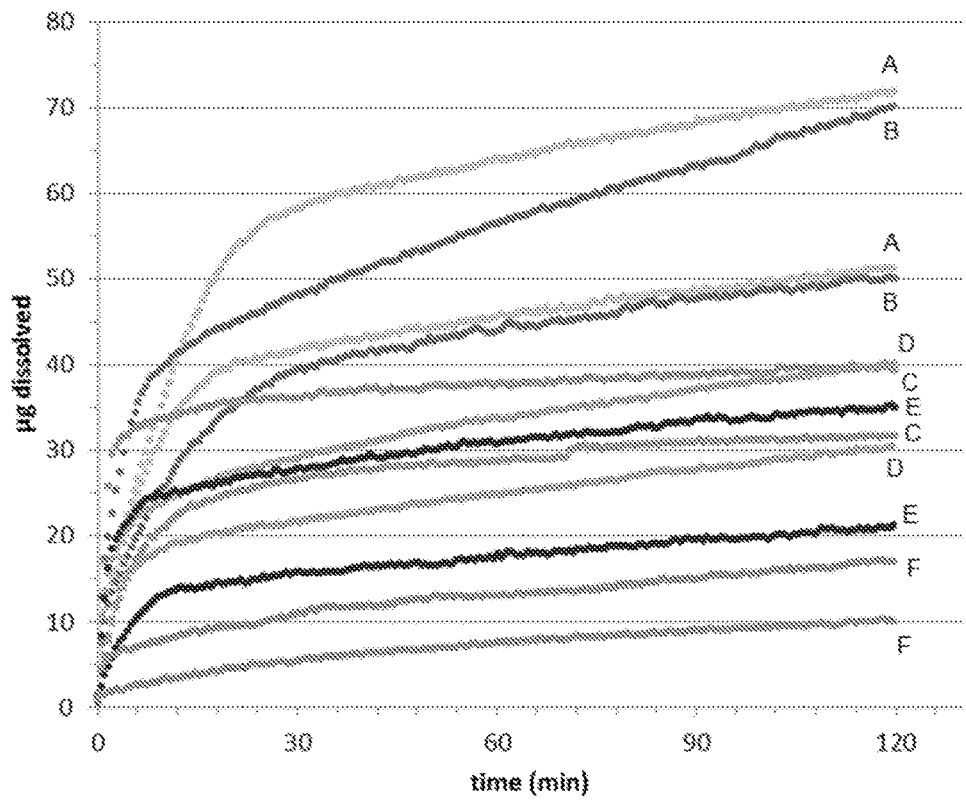
FIG. 9 shows the intrinsic dissolution of free base (F), ethane-1,2-disulfonate (E), hydrobromide (D), hydrochloride (C), benzenesulfonate (B) and p-toluenesulfonate (A) salts of RPL554.

The results of the dissolution experiments are shown in FIGS. 8 and 9. Every compound was measured in duplicate. Note that FIG. 8 shows the compound released in milligrams and FIG. 9 shows the compound released in micrograms.

The intrinsic dissolution rates of the salts are shown in Table 12.

TABLE 12

| Salt | Mass of salt (µg) dissolved after 2 hours | | |
| --- | --- | --- | --- |
| | Test 1 | Test 2 | Average |
| sulfate salt | 5910 | 6500 | 6205 |
| ethanesulfonate salt | 300 | 410 | 355 |
| methanesulfonate salt | 160 | 290 | 225 |
| p-toluenesulfonate salt | 51.2 | 71.9 | 61.6 |
| benzenesulfonate salt | 50.0 | 70.1 | 60.1 |
| hydrochloride salt | 31.7 | 39.4 | 35.6 |
| hydrobromide salt | 30.4 | 40.1 | 35.3 |
| ethane-1,2-disulfonate salt | 21.1 | 34.9 | 28.0 |
| free base | 10.0 | 17.0 | 13.5 |

The dissolution plots shows that all salts dissolved in a greater amount than the free base after 2 hour experiments at the same conditions. Three salts; sulfate, methanesulfonate and ethanesulfonate, showed higher dissolution than the rest of the salts as is shown in FIG. 8. It should be noted that the maximum pH change (from a nominal start pH of pH7) was about 0.15 pH units decrease, which was for the sulfate salt. The methanesulfonate was about 0.1 pH units decrease. The rest of the salts decreased by less than 0.06 pH units.

In FIG. 9 the free base was plotted with the five other salts (ethane-1,2-disulfonate, HBr, HCl, benzenesulfonate and p-toluenesulfonate) and showed less amount of sample released for the same experiments.

Particular behaviour observed for the methanesulfonate salt showed a high release in the first 20 minutes, with 3960 µg dissolved at 8.5 min and 5200 µg dissolved at 11 min, followed by precipitation (FIG. 8). The ethanesulfonate showed a less pronounced initial peak in dissolution (600 µg at 5.7 min and 700 µg at 13 min).

Figure 10:
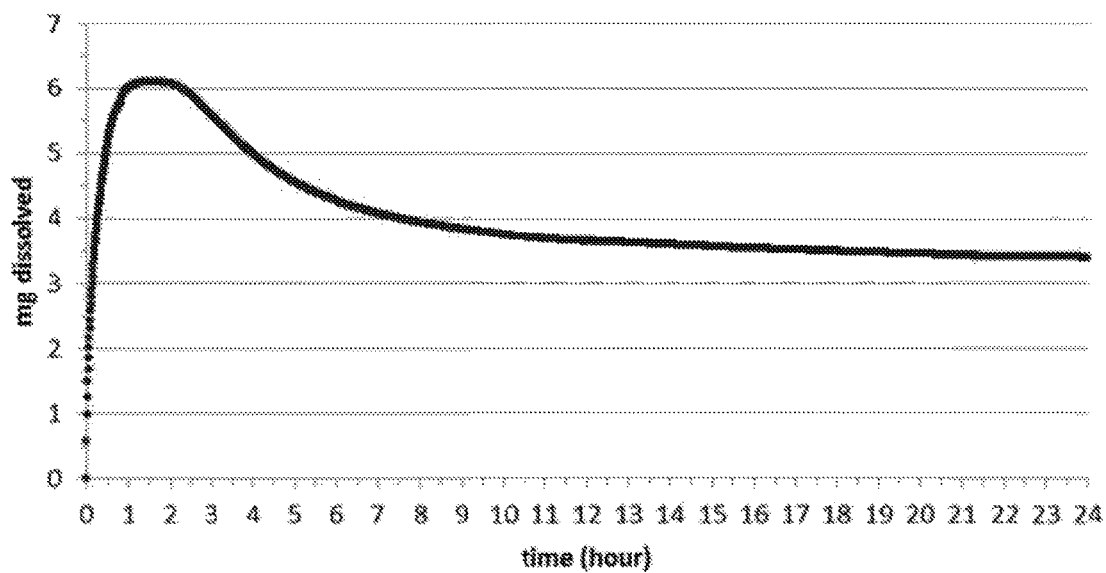
FIG. 10 shows the intrinsic dissolution of the sulfate salt of RPL554 over 24 hours.

The sulfate salt showed a high release initially and it was expected that this sample would also precipitate if given enough time; hence another experiment was performed increasing the time of the experiment to 24 hours (FIG. 10). The behaviour observed in FIG. 10 was similar to the previous sulfate salt experiments for the first two hours. Thereafter, the sample did start to precipitate slowly but still remained highly supersaturated even after 24 hrs.

The salts of RPL554 were shown to all have improved intrinsic dissolution rates compared with free base, with some salts (sulfate, methanesulfonate and ethanesulfonate) showing particularly high dissolution rates.

Enhanced dissolution rates of the salts could potentially greatly increase both the speed and extent of drug availability in the lung from pMDI, DPI and nevulised suspension formulations. This could facilitate the modulation of pharmacokinetics of the drug to change both the onset and duration of activity. The more rapid dissolution without changing the pH of the buffer system indicates this dissolution could occur without potential irritation of the lung which might be induced by lower pH formulations.

Example 8—Evaluation of RPL554 and Salt Variations in pMDI and DPI Formulations

Methods

HPLC Assay Analysis

A validated high performance liquid chromatography (HPLC) method (Intertek Melbourn scientific analytical method AM/358/01) for the determination of the aerodynamic droplet size distribution of RPL554 suspensions for nebulisation was used.

The assay was performed using an Agilent (Agilent Technologies Ltd, UK) 1200 series HPLC system consisting of: isocratic pump, variable wavelength detector, autosampler, thermostatted column compartment and utilised Chemstation LC software, Rev. B04.02.

The following chromatography conditions were used: Column: Waters X Bridge phenyl, 3.5 µm, 150×4.6 mm, (Part number 186003335); Diluent: Acetonitrile:Water (50: 50, v/v); Mobile Phase: Acetonitrile: Water: Trifluoroacetic acid (45:55:1 (v/v)); Flow Rate: 1.5 mL/min; Injection Volume: 10 µL; Detection: UV @ 254 nm; Column Temperature: 40° C.; Autosampler Tray Temperature: Ambient; Run Time: 6 minutes.

HPLC Stability Analysis

A validated HPLC method (Onyx-Scientific, Final product testing monograph for RPL554) for the determination of chemical purity by HPLC was used.

The assay was performed using an Agilent (Agilent Technologies Ltd, UK) 1200 series HPLC system consisting of: Quaternary Pump, Multiple Wavelength Detector, Autosampler, Thermostatted Column Compartment, Degasser and utilised Chemstation LC Software Rev. B.04.02

The following chromatography conditions were used: Column: Waters X Bridge phenyl, 3.5 µm, 150×4.6 mm, (Part number 186003335); Diluent: Acetonitrile:Water (50:

50, v/v); Mobile Phase: A—Purified Water:Trifluoroacetic acid (100:0.1); B—Acetonitrile:Trifluoroacetic acid (100:0.1); Flow Rate: 1.0 mL/min; Injection Volume: 10 μl; Detection: UV @ 254 nm; Column Temperature: 30° C.; Post Run: 5 min; Gradient: [Time (min): % A:% B]: [0:95:5], [2:95:5], [15:5:95], [20:5:95], [22:95:5].

Primary Particle Size Analysis

A Mastersizer 2000 fitted with a Scirocco 2000 dry powder dispersion unit (Malvern Instruments Ltd, UK) was used to analyse the primary particle size of the micronised RPL554 and salt variants. The salts (50 mg) were automatically sampled via a vibrating feed control at a feeder rate of 60% and dispersed in compressed air at a pressure of 3 bar.

Visual inspection of the compounds indicated that the powders demonstrated a degree of cohesive behaviour, with small aggregates existing within the mass of powder. However, there was no need to further de-aggregate these before analyses.

pMDI Manufacture pMDI formulations containing a 6 mL fill of either HFA 134a, HFA 227 or 50:50 w/w blend of HFA 134a: 227 were prepared in 19 mL PET bottles. Each PET bottle contained 24 mg of RPL554 or salt variation, and was sealed with a 50 μL KHFA valve to provide 200 μg salt/actuation. Due to differences in the molecular weights of the RPL554 salt forms, the amount of RPL554 base equivalent emitted per actuation varied as a function of the molecular weight of each salt. The formulations were prepared with no adjustment for differences in molecular weight of the salts.

For each propellant and for the propellant blend, pMDI's were also formulated to contain 10% (w/w) absolute ethanol containing 0.1% (w/w) Tween® 80 (referred to as ethanol/Tween). The formulation constituents are shown in the tables below.

| HFA 134a | Per Canister | | | |
|---|---|---|---|---|
|  | mL | g | % w/w | % w/w (ex-drug) |
| HFA 134a | 6.0000 | 7.3080 | 99.6727 | 100.0000 |
| HFA 277ea |  |  |  |  |
| Ethanol |  |  |  | 0.0000 |
| Tween 80 |  |  |  | 0.0000 |
| RPL554 Salt |  | 0.0240 | 0.3273 |  |
| Totals | 6.0000 | 7.3320 | 100.0000 |  |

| HFA 134a 10% Ethanol | Per Canister | | | |
|---|---|---|---|---|
|  | mL | g | % w/w | % w/w (ex - drug) |
| HFA 134a | 5.3940 | 6.5699 | 89.6057 | 89.900 |
| HFA 227ea |  |  |  |  |
| Ethanol | 0.9276 | 0.7308 | 9.9673 | 10.000 |
| Tween 80 | 0.0069 | 0.0073 | 0.0997 | 0.100 |
| RPL554 Salt |  | 0.0240 | 0.3273 |  |
| Totals | 6.3216 | 7.3320 | 100.0000 |  |

| HFA134a:HFA 227a | Per Canister | | | |
|---|---|---|---|---|
|  | mL | g | % w/w | % w/w (ex - drug) |
| HFA 134a | 3.0000 | 3.6540 | 46.3823 | 46.5241 |
| HFA 227ea | 3.0000 | 4.2000 | 53.3130 | 53.4759 |
| Ethanol |  |  |  | 0.0000 |
| Tween 80 |  |  |  | 0.0000 |
| RPL554 Salt |  | 0.0240 | 0.3046 |  |
| Totals | 6.0000 | 7.8780 | 100.0000 |  |

| HFA134a:HFA 227a 10% Ethanol | Per Canister | | | |
|---|---|---|---|---|
|  | mL | g | % w/w | % w/w (ex - drug) |
| HFA 134a | 2.6970 | 3.2849 | 41.6977 | 41.8251 |
| HFA 227ea | 2.6970 | 3.7758 | 47.9284 | 48.0749 |
| Ethanol | 0.9970 | 0.7854 | 9.9695 | 10.0000 |
| Tween 80 | 0.0074 | 0.007854 | 0.0997 | 0.1000 |
| RPL554 Salt |  | 0.0240 | 0.3046 |  |
| Totals | 6.3910 | 7.8780 | 100.0000 |  |

| HFA 227a | Per Canister | | | |
|---|---|---|---|---|
|  | mL | g | % w/w | % w/w (ex - drug) |
| HFA 134a |  |  |  |  |
| HFA 227ea | 6.0000 | 8.4000 | 99.7151 | 100.0000 |
| Ethanol |  |  |  | 0.0000 |
| Tween 80 |  |  |  | 0.0000 |
| RPL554 Salt |  | 0.0240 | 0.2849 |  |
| Totals | 6.0000 | 8.4240 | 100.0000 |  |

| HFA 227a 10% Ethanol | Per Canister | | | |
|---|---|---|---|---|
|  | mL | g | % w/w | % w/w (ex - drug) |
| HFA 134a |  |  |  |  |
| HFA 227ea | 5.3940 | 7.5516 | 89.6439 | 89.9000 |
| Ethanol | 1.0663 | 0.8400 | 9.9715 | 10.0000 |
| Tween 80 | 0.0079 | 0.0084 | 0.0997 | 0.1000 |
| RPL554 Salt |  | 0.0240 | 0.2849 |  |
| Totals | 6.4603 | 8.4240 | 100.0000 |  |

The stock solution of Tween 80 in absolute ethanol was prepared at a concentration of 1% w/w. Thus the addition of small amounts of Tween® 80 required for the formulations was achieved by the use of the ethanol/Tween solutions as shown in the above tables.

In total 54 pMDI samples were prepared.

Visual Assessment of pMDI Formulations

Preliminary assessments of the physical properties of the pMDI formulations were based on visual indicators i.e. solubility, flocculation, sedimentation and creaming.

The information relating to assessment of physical properties was recorded in the form of digital photographic images. Digital pictures of the pMDI bottles were recorded immediately after shaking the formulations, and thereafter at intervals over a period of up to 3 minutes, images were also taken after the contents of the PET bottles had been left undisturbed in excess of five minutes. Furthermore the ease and extent of dispersion, flocculation, and the sedimentation (or creaming) rate and sedimentation (or creaming) height were also scored.

Based on the results of the physical assessment, six formulations were selected for aerosol characterisation tests.

Solubility Measurements of RPL554 and Salts in Selected pMDI Formulations

Quantitative assessment of the solubility of RPL554 and salt variants in the propellant systems of selected pMDI formulations (three replicates of each formulation) was performed.

pMDIs were directly coupled to an adaptor fitted with a 0.20 μm filter unit connected, in series to a 21 G needle, which was inserted via a rubber septum, into a cooled multi-dose glass vial. A 19 G filter needle was inserted through the septum to aid evaporation of propellant from the vial. Prior to the filtration process the vial was cooled in a mixture of dry ice and acetone to ensure that the pressure within the vial was reduced in order to facilitate collection of the output from the pMDI. Ten consecutive actuations of the pMDI were fired through the filter and collected in the vial. Between actuations the canister was shaken for approximately 10 seconds. The pMDI unit was weighed before and after the filtering procedure. The filtrate was stored at room temperature and allowed to evaporate to dryness.

Samples were recovered by carefully rinsing the inside of the vials with 1 mL of recovery solution before transfer to HPLC vials for analysis. The estimated % of RPL554 solubilised within the canister was calculated from the starting mass of RPL554 within the canisters, which in turn was calculated using the theoretical molecular weight values of the RPL554 free base and salt variants shown in Table 13. The theoretical molecular weight estimates of the salts were provided by Verona. (All were considered as 1:1 stoichiometric salts, except for the ethane-1,2-disulfonate which was confirmed to be a hemi-salt.)

TABLE 13

| RPL554 Variant | Theoretical Molecular Weights | Calculated mass of RPL554 base within canister (mg) | Calculated metered dose (μg) RPL554 base per actuation |
|---|---|---|---|
| Free Base | 477.56 | *24.0 | 200 |
| Ethanesulfonate | 587.69 | 19.5 | 163 |
| p-Toluenesulfonate | 649.78 | 17.6 | 147 |
| Methanesulfonate | 573.67 | 20.0 | 166 |
| Benzenesulfonate | 635.74 | 18.0 | 150 |
| Sulfate | 575.64 | 19.9 | 166 |
| Hydrochloride | 514.02 | 22.3 | 186 |
| Ethane-1,2-disulfonate | 572.65 | 20.0 | 167 |
| Hydrobromide | 558.47 | 20.5 | 171 |

Aerosol Characterisation Tests of pMDI Formulations

Inertial impaction tests were performed using the Next Generation Impactor (NGI) under standard conditions i.e. 30 L/min flow rate, with the addition of a final external filter, to capture RPL554 variant that may have been solubilised. The emitted dose (ED, μg), fine particle dose (FPD, μg) and fine particle fraction (FPF, %) were evaluated. The assessments were performed at the beginning of canister life, and 5 consecutive actuations were fired into the NGI using a 0.25 mm orifice diameter actuator (NMX). Between actuations the canister was removed from the NGI inlet and shaken for approximately 15 seconds. RPL554 was quantitatively recovered from the actuator, induction port, each of the NGI collection stages and the external filter with 10 mL of diluent. The volume of diluent (50% acetonitrile in HPLC grade water) used for each sample was selected to ensure RPL554 concentrations were above the limits of quantitation of the HPLC assay method (0.06 μg/mL).

Dry Powder Inhaler RPL554 Free Base and Salt:Lactose Powder Blends

RPL554 and salt variations were prepared as DPI formulations using lactose as the excipient.

Batches (approximately 5 g) of 1% w/w RPL554 free base or salt variants: lactose blends were prepared. In brief, the RPL554 free base or salt plus a small quantity of lactose was passed through a 38 μm sieve. The sieved material plus the remaining lactose was mixed in a glass mortar prior to transfer to a stainless steel screw cap jar and further mixing (10 minutes at 46 rpm) conducted using a Turbula blender. The composition of the dry powder blend was 0.05 g API and 4.95 g lactose.

In order to determine the content uniformity of the blends, aliquots (approx. 20 mg) of powder were sampled from each blend, accurately weighed, and diluted to volume in 10 mL volumetric flasks with diluent. The flasks were sonicated for 3 minutes before samples were transferred to HPLC vials for analysis.

Aerosol Performance of DPI Formulations

Capsules were hand filled with 20 mg of the 1% w/w RPL554 free base or salt variants: lactose blends, i.e. 200 μg salt per capsule, the fill weight of each capsule was recorded. Due to differences in the molecular weights of the RPL554 salt forms, the amount of RPL554 emitted per actuation varied as a function of molecular weight. The formulations were prepared with no adjustment for differences in molecular weight of the salts.

The powders were delivered via the Cyclohaler DPI (PCH Pharmachemie, BV, The Netherlands). The Cyclohaler® DPI is a low resistance device and was operated at a flow rate of 90 L/min for 2.7 seconds. The cut off diameters for the NGI collection stages were calculated for the 90 L/min flow rate using the NGI User Guide (MSP Corporation, 2008).

The ED, FPD and FPF were determined from inertial impaction tests performed following the deposition of 5 capsules of each formulation into the NGI. For each capsule tested the combined weight of the Cyclohaler® and capsule was determined before and after operation to check that the dose had been delivered. The NGI was fitted with a pre-separator for these determinations. The central cup of the pre-separator was filled with 15 mL of diluent. Following deposition, the solution was recovered in a 20 mL volumetric flask and made up to volume with diluent. RPL554 was quantitatively recovered from the device, induction port and each of the NGI collection stages with 10 mL of diluent.

The volume of diluent used for each sample was selected to ensure RPL554 concentrations were above the limit of quantitation.

Stability Assessment of RPL554 and Salts: Lactose Powder Blends

Samples of 1% w/w RPL554 free base or salt variants: lactose blends were prepared and stored at elevated temperature (70° C.) for seven days, control samples were stored at ambient conditions and protected from light on the laboratory bench. All samples (approximately 0.5 g) were accurately weighed into screw cap glass scintillation vials (20 mL). For storage at elevated temperature samples were placed in an oven at 70° C. protected from light. Control sample vials were capped, protected from light and stored on the bench for 7 days.

In addition, to the RPL554 and salt variant blends, samples of lactose alone were also stored at the elevated temperature condition (control samples at ambient). The lactose only samples served as baseline data for the HPLC analysis. HPLC traces produced from the lactose only samples were subtracted from the traces in order to account for non-drug associated peaks.

Results and Discussions

Primary Particle Size Analysis

Table 14 shows the particle size distribution of the micronised RPL554 and salt variants as measured using laser light diffraction and shown as mean values, n=3 measurements. The results indicated that the salts were suitably micronised for formulation as a respiratory product, all D(0.9) values were less than 5 µm.

TABLE 14

| RPL554 Variant | D (0.1) (µm) | D (0.5) (µm) | D (0.9) (µm) |
|---|---|---|---|
| Free base | 0.58 | 1.37 | 3.00 |
| Ethanesulfonate | 0.56 | 1.43 | 4.18 |
| p-Toluenesulfonate | 0.47 | 1.34 | 4.53 |
| Methanesulfonate | 0.45 | 1.20 | 3.46 |
| Benzenesulfonate | 0.46 | 1.23 | 3.51 |
| Sulfate | 0.51 | 1.12 | 2.30 |
| Hydrochloride | 0.53 | 1.37 | 3.47 |
| Ethane-1,2 disulfonate | 0.52 | 1.25 | 2.78 |
| Hydrobromide | 0.64 | 1.52 | 3.23 |

Pressurised Metered Dose Inhaler Assessments

Visual Assessment of pMDI Formulations pMDI formulations of each RPL554 free base and salt variant for each of the different combinations of propellant (HFA 134a, HFA 227 or 50:50 (w/w) HFA 134a: 227), ethanol/Tween were scored in terms of dispersibility, flocculation, sedimentation (or creaming) rate and sedimentation (or creaming) height and based on these observations the potential of suitability for formulation as pMDI.

For the visually assessed variables, many of the formulations displayed very similar characteristics.

It was decided, that in addition to the RPL554 free base in 50:50 propellant containing ethanol/Tween the remaining chosen pMDI formulations to be assessed by inertial impaction analysis were as follows:
1. RPL554 free base HFA 134a/227 and ethanol/Tween
2. RPL554 ethanesulfonate HFA 227
3. RPL554 methanesulfonate HFA 134a
4. RPL554 benzenesulfonate HFA 134a
5. RPL554 sulfate HFA 134a
6. RPL554 ethane-1,2-disulfonate HFA 227 and ethanol/Tween Solubility Measurements of RPL554 Free Base and Salts in Selected pMDI Systems The solubilities of the RPL554 free base and 8 salt variants in HFA 134a are shown in Table 15. From the visual assessments, none of the formulations demonstrated clear signs of solubility within the propellant. However, from the results of solubility testing, the ethanesulfonate and p-toluenesulfonate salts demonstrated quantifiable levels of solubility.

The solubilities of the RPL554 free base and 8 salt variants in HFA 134a and ethanol/Tween are shown in Table 16. From the visual assessments, some of the formulations demonstrated signs of solubility within the propellant. The solubility testing of the formulations demonstrated that the addition of ethanol/Tween had an effect on the solubility of RPL554 within the propellant. All formulations demonstrated detectable levels of solubility, ranging from the lowest with ethane-1,2-disulfonate (5 µg/g) to the highest with methanesulfonate (298 µg/g).

The solubility of the RPL554 free base and 8 salt variants in HFA 227 was assessed, however, there were no quantifiable levels within the samples (Table 17).

Further solubility measurements were performed for two formulations that demonstrated interesting physical properties for selection as candidates for inertial impaction tests. Table 18 illustrates the quantifiable levels of RPL554 solubility for ethane-1,2 disulfonate in HFA 227 and ethanol/Tween and for the free base in HFA 134:227 and ethanol/Tween. In both cases, the fraction of solubilised RPL554 represented less than 1% of the drug present in the formulation.

TABLE 15

Solubility in HFA 134

| RPL554 Variant | Solubility RPL554 (µg/g) | Calculated Solubilised RPL554 µg per 50 µL actuation | Calculated RPL554 solubilised (%) |
|---|---|---|---|
| Free Base | BLQ | BLQ | BLQ |
| Ethanesulfonate | 126.81 | 9.03 | 5.56 |
| p-Toluenesulfonate | 1.56 | 0.11 | 0.08 |
| Methanesulfonate | BLQ | BLQ | BLQ |
| Benzenesulfonate | BLQ | BLQ | BLQ |
| Sulfate | BLQ | BLQ | BLQ |
| Hydrochloride | BLQ | BLQ | BLQ |
| Ethane-1,2-disulfonate hemi-salt | BLQ | BLQ | BLQ |
| Hydrobromide | BLQ | BLQ | BLQ |

*BLQ—below limit of quantitation (0.06 µg/mL)

TABLE 16

Solubility in HFA 134 with Ethanol/Tween

| RPL554 Variant | Solubility RPL554 (µg/g) | Estimated Solubilised RPL554 µg per 50 µL actuation | Estimated RPL554 solubilised (%) |
|---|---|---|---|
| Free Base | 16.45 | 1.12 | 0.56 |
| Ethanesulfonate | 266.59 | 17.81 | 10.96 |
| p-Toluenesulfonate | 152.85 | 10.58 | 7.20 |
| Methanesulfonate | 298.07 | 19.38 | 11.64 |
| Benzenesulfonate | 90.57 | 6.05 | 4.03 |
| Sulfate | 73.19 | 4.71 | 2.84 |
| Hydrochloride | 149.17 | 9.79 | 5.27 |
| Ethane-1,2-disulfonate hemi-salt | 5.13 | 0.34 | 0.20 |
| Hydrobromide | 96.27 | 6.40 | 3.74 |

TABLE 17

Solubility in HFA 227

| RPL554 Variant | Solubility RPL554 (µg/g) | Calculated Solubilised RPL554 µg per 50 µL actuation | Calculated RPL554 solubilised (%) |
|---|---|---|---|
| Free Base | BLQ | BLQ | BLQ |
| Ethanesulfonate | BLQ | BLQ | BLQ |
| p-Toluenesulfonate | BLQ | BLQ | BLQ |
| Methanesulfonate | BLQ | BLQ | BLQ |

TABLE 17-continued

Solubility in HFA 227

| RPL554 Variant | Solubility RPL554 (µg/g) | Calculated Solubilised RPL554 µg per 50 µL actuation | Calculated RPL554 solubilised (%) |
|---|---|---|---|
| Benzenesulfonate | BLQ | BLQ | BLQ |
| Sulfate | BLQ | BLQ | BLQ |
| Hydrochloride | BLQ | BLQ | BLQ |
| Ethane-1,2-disulfonate hemi-salt | BLQ | BLQ | BLQ |
| Hydrobromide | BLQ | BLQ | BLQ |

TABLE 18

| RPL554 Variant | Solubility RPL554 (µg/g) | Estimated Solubilised RPL554 µg per 50 µL actuation | Estimated RPL554 solubilised (%) |
|---|---|---|---|
| Ethane-1,2-disulfonate hemi-salt - HFA 227:10% Ethanol:0.1% Tween | 1.69 | 0.11 | 0.07 |
| Free base - HFA 134a:227:10% Ethanol:0.1% Tween | 16.11 | 1.06 | 0.53 |

Inertial Impaction Testing of pMDI Formulations

Figure 11:
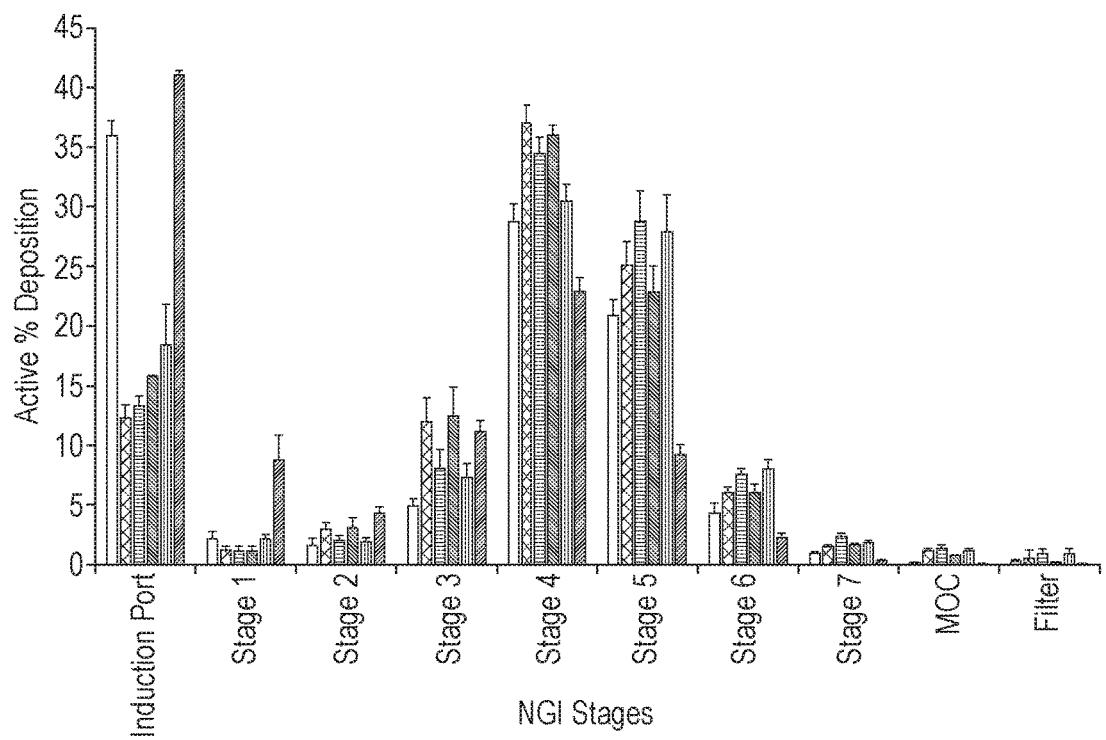
FIG. 11 shows the aerodynamic assessment of selected RPL554 base and salt pMDI formulations (mean values, n=3, ±SD), where the bars from left to right are: free base 134/227 10% EtOH; ethanesulfonate 227; methanesulfonate 134a; benzenesulfonate 134a; sulfate 134a; and ethanedisulfonate 227 10% EtOH.

FIG. 11 shows the recovery of the pMDI formulations following collection in the NGI. Deposition was promising with large amounts of material displaying aerodynamic properties suitable for inhalation, FPF values (i.e. % particles<5 µm ex-actuator) ranged from 48.2 to 81.0%, with methanesulfonate in HFA 134a displaying the highest FPF. The Induction Port (inlet throat) deposition was predominantly less than 20%, with the exception of the free base (50:50 propellant with ethanol/Tween) and ethane-1,2-disulfonate (HFA 227 with ethanol/Tween) formulations.

The mean metered doses in Table 19 (mean values, n=3, ±SD) shows the RPL554 recovery ranged from 53-75% of the theoretical metered dose (assuming no adsorption) shown in Table 13.

TABLE 19

| RPL554 Variant | Free base | Ethane-sulfonate | Methane-sulfonate |
|---|---|---|---|
| Metered Weight (mg) | 66.18 ± 0.2 | 77.56 ± 0.2 | 70.29 ± 0.7 |
| Metered dose per Actuation (µg) | 138.60 ± 1.6 | 105.28 ± 1.4 | 105.71 ± 2.9 |
| % of Free Base on Actuator | 6.97 ± 0.6 | 11.06 ± 1.5 | 10.29 ± 0.8 |
| Emitted Dose per Actuation (µg) | 128.93 ± 0.8 | 93.65 ± 2.7 | 94.84 ± 2.9 |
| FPF (% <5 µm) | 60.22 ± 1.6 | 79.66 ± 2.0 | 81.02 ± 1.6 |
| MMAD (µm) | 1.35 ± 0.1 | 2.20 ± 0.1 | 1.84 ± 0.1 |
| GSD | 2.62 ± 0.1 | 1.99 ± 0.1 | 2.11 ± 0.02 |
| FPD (µg <5 µm) | 77.63 ± 2.1 | 74.59 ± 2.5 | 76.81 ± 1.6 |

| RPL554 Variant | Benzene-sulfonate | Sulfate | Ethane-1,2-Disulfonate |
|---|---|---|---|
| Metered Weight (mg) | 72.69 ± 0.1 | 70.08 ± 0.2 | 66.71 ± 0.2 |
| Metered dose per Actuation (µg) | 112.48 ± 2.6 | 87.24 ± 1.4 | 107.41 ± 1.6 |
| % of Free Base on Actuator | 9.13 ± 0.4 | 8.03 ± 1.5 | 6.77 ± 0.2 |
| Emitted Dose per Actuation (µg) | 102.21 ± 2.3 | 80.25 ± 2.3 | 100.14 ± 1.2 |
| FPF (% <5 µm) | 76.41 ± 2.0 | 75.69 ± 3.4 | 48.15 ± 1.2 |
| MMAD (µm) | 2.20 ± 0.2 | 1.60 ± 0.1 | 1.84 ± 0.1 |
| GSD | 1.99 ± 0.04 | 2.44 ± 0.03 | 3.48 ± 0.3 |
| FPD (µg <5 µm) | 78.08 ± 2.3 | 60.74 ± 3.2 | 48.21 ± 0.8 |

RPL554 Free base in 50:50 propellant and ethanol/Tween; RPL554 Ethanesulfonate in HFA 227; RPL554 Methanesulfonate, Benzenesulfonate and Sulfate in HFA 134a and RPL554 Ethane-1,2-disulfonate in HFA 227 and ethanol/Tween.

Dry Powder Inhaler Assessments

Single batches containing 1% w/w of RPL554 free base or salt: lactose were prepared.

Samples of each blend were tested to determine the RPL554 base content and the aerodynamic properties of each blend were also tested. Samples of the preparations were also stored at elevated temperature (70° C.) for seven days to assess stability.

Dry Powder Inhaler RPL554 Free Base and Salt: Lactose Powder Blends

The RPL554: lactose powder blends were prepared under temperature and humidity conditions of 17° C. and 56% RH. The measured RPL554 content of blends demonstrated close agreement with the theoretical content, as shown in Table 20, (calculated from molecular weights in Table 13) for the free base, ethanesulfonate and methanesulfonate (mean values, n=3, ±SD). The remaining blends, with the exception of the sulfate, gave values between 80 and 90% of the theoretical values. The lower figure for the sulfate salt reflects the lower purity of the input material (known to contain an impurity at a level of ~15% area by HPLC-UV). However, all the blends were found to have content uniformity of less than 5% RSD and therefore deemed suitable for further testing, given that the purity and water content of the salts were not known at the date of testing.

TABLE 20

| RPL554 Variant | Total RPL554 Recovered (µg) | Theoretical RPL554 Content µg (1% w/w) | Recovered RPL554 Content (% Theoretical) |
|---|---|---|---|
| Base | 194.17 ± 3.2 | 201.33 ± 1.5 | 96.44 ± 0.9 |
| Ethanesulfonate | 161.89 ± 2.4 | 163.88 ± 0.5 | 98.79 ± 1.3 |
| p-Toluene-sulfonate | 130.98 ± 1.9 | 147.73 ± 0.7 | 88.66 ± 1.1 |
| Methanesulfonate | 165.05 ± 2.9 | 166.49 ± 0.0 | 99.13 ± 1.7 |
| Benzenesulfonate | 134.89 ± 1.2 | 150.99 ± 0.8 | 89.34 ± 0.5 |
| Sulfate | 122.77 ± 2.8 | 167.03 ± 1.0 | 73.50 ± 1.3 |
| Hydrochloride | 158.44 ± 4.4 | 187.67 ± 1.9 | 84.42 ± 1.9 |
| Ethane-1,2-disulfonate | 135.96 ± 3.0 | 169.57 ± 0.5 | 80.18 ± 1.6 |
| Hydrobromide | 143.99 ± 0.6 | 172.73 ± 2.3 | 83.37 ± 0.8 |

Aerosol Performance of DPI Formulations

The weight of the Cyclohaler® plus capsule was determined before and after each dose was delivered in order to estimate the total mass of powder blend delivered for each NGI determination. The total delivered doses estimated from weight measurements are shown in Table 21 (5 capsules containing 20 mg of powder blend (200 µg free base or salt/capsule)) via Cyclohaler®; all values expressed as RPL554 base except *). The table also shows the calculation of the masses of RPL554 base delivered for each RPL554 variant. This figure was adjusted to take into account the actual RPL554 base content (i.e. % theoretical) of each of the blends. The total µg of recovered RPL554 base, determined by HPLC analysis of samples from the NGI is also shown. Mass balance i.e. actual recovery (HPLC analysis)/calculated recovery (mass measurements) indicated that for all 9 formulations 64-74% recovery was achieved.

TABLE 21

| RPL554 Variant | *Theoretical µg RPL554 Variant per 20 mg of 1% w/w Blend | Theoretical µg RPL554 per 20 mg, 1% w/w Blend in each capsule | Measured Blend Content (% Theoretical) | **Adjusted RPL554 Content per capsule (µg) |
|---|---|---|---|---|
| Free Base | 200 | 200.00 | 96.44 | 192.87 |
| Ethanesulfonate | 200 | 162.52 | 98.79 | 160.55 |
| p-Toluene-sulfonate | 200 | 146.99 | 88.66 | 130.33 |
| Methanesulfonate | 200 | 166.49 | 99.13 | 165.05 |
| Benzenesulfonate | 200 | 150.24 | 89.34 | 134.22 |
| Sulfate | 200 | 165.92 | 73.50 | 121.95 |
| Hydrochloride | 200 | 185.81 | 84.42 | 156.86 |
| Ethane-1,2-disulfonate | 200 | 166.79 | 80.18 | 133.73 |
| Hydrobromide | 200 | 171.02 | 83.37 | 142.58 |

| RPL554 Variant | †Measured Mass of 1% w/w Blend Delivered per capsule (mg) | Calculated RPL554 Content (µg) per capsule (A) | ††RPL554 Emitted (µg) per capsule (B) | % Recovery (B/A) |
|---|---|---|---|---|
| Free Base | 20.12 | 194.03 | 133.59 | 68.85 |
| Ethanesulfonate | 20.18 | 162.00 | 111.09 | 68.57 |
| p-Toluene-sulfonate | 20.02 | 130.46 | 86.84 | 66.57 |
| Methanesulfonate | 19.96 | 164.72 | 118.69 | 72.06 |
| Benzenesulfonate | 20.04 | 134.49 | 87.57 | 65.11 |
| Sulfate | 19.78 | 120.61 | 79.35 | 65.79 |
| Hydrochloride | 20.14 | 157.96 | 102.27 | 64.75 |
| Ethane-1,2-disulfonate | 19.90 | 133.06 | 87.91 | 66.07 |
| Hydrobromide | 19.96 | 142.29 | 104.28 | 73.29 |

Figure 12:
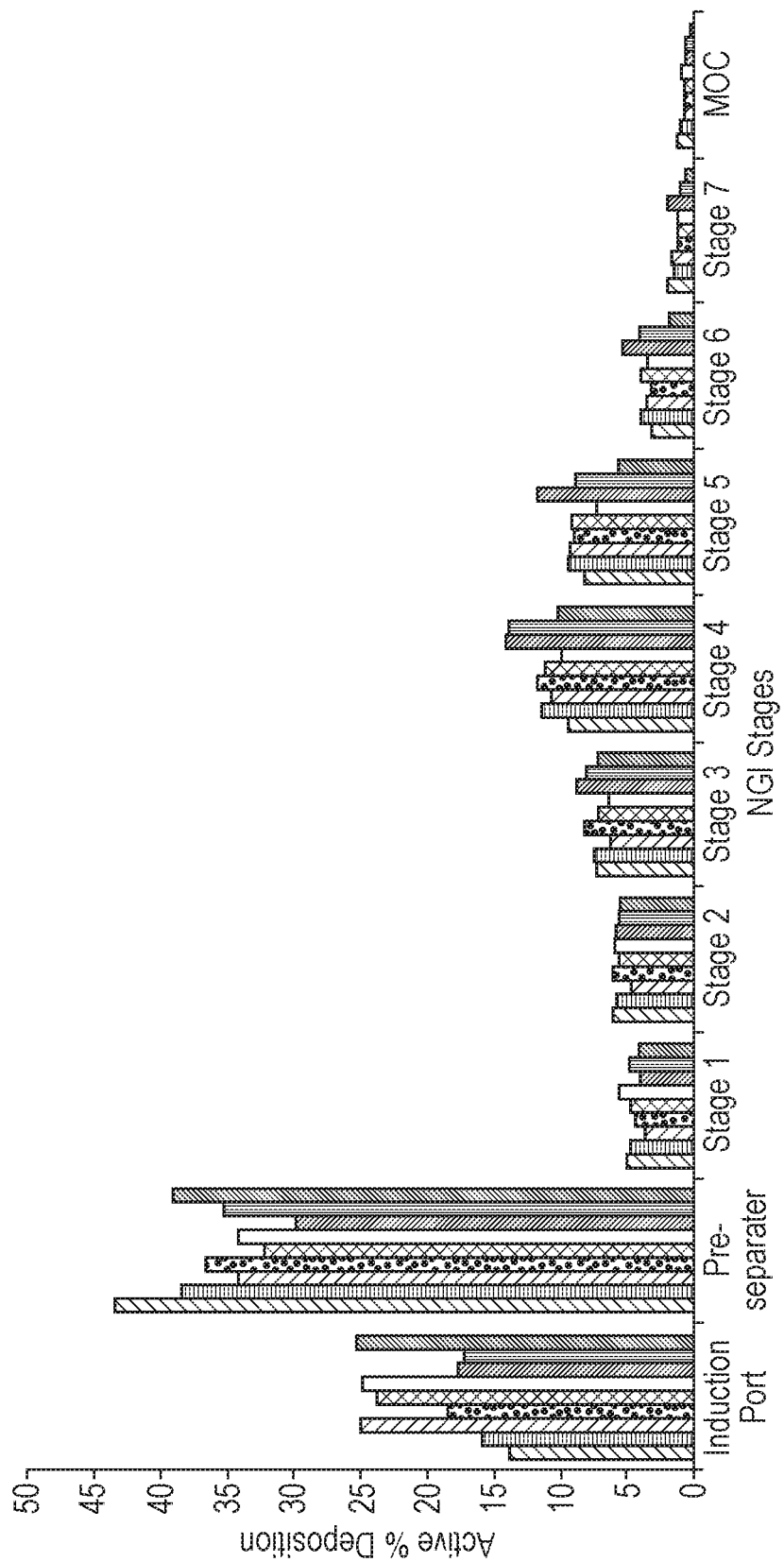
FIG. 12 shows the aerodynamic assessment of RPL554 free base and salt variant DPI formulations, where the bars from left to right are: free base; ethanesulfonate; p-toluenesulfonate; methanesulfonate; benzenesulfonate; sulfate; hydrochloride; ethane-1,2-disulfonate; and hydrobromide.

**Adjusted for measured blend content (% theoretical - see Table 3.4.1.1)
†Mass determined from weight change of capsule-loaded device
††Mass determined from HPLC analysis of recovered samples The particle size distributions of free base and salts aerosolised using the Cyclohaler are shown in FIG. 12 and summaries of the key performance indicators are shown in Table 22 (formulated as 1% w/w lactose blends and delivered via the Cyclohaler® DPI; five capsules each containing 20 mg of powder blend (200 µg RPL554 variant/capsule) were used for each determination).

The minimum FPF was observed for the hydrobromide formulation (29.43%); for all other blends the FPF exceeded 30%, with a maximum value of 46.29% determined for the hydrochloride salt. The minimum fine particle dose (RPL554 base equivalent) was 23.28 for the sulfate salt formulation, while the maximum was 43.31 µg for the free base blend, reflecting the differences in the metered dose (and in the case of the sulfate salt, additionally the lower purity of the input material). MMAD values were within the range of 1.72 µm to 2.31 µm.

TABLE 22

| RPL554 Variant | FB | ES | PT | MS | BS |
|---|---|---|---|---|---|
| Recovered RPL554 base/Capsule (ex-capsule) (µg) | 133.59 | 111.09 | 86.84 | 118.69 | 87.57 |
| Emitted Dose of RPL554 base/Capsule (ex-device) (µg) | 123.05 | 100.75 | 77.79 | 111.01 | 77.30 |
| FPF (% <5 µm) | 35.20 | 38.70 | 35.37 | 38.18 | 36.99 |
| MMAD (µm) | 1.99 | 1.87 | 1.74 | 2.00 | 1.91 |
| GSD | 2.63 | 2.57 | 2.55 | 2.40 | 2.57 |
| FPD RPL554 base (µg <5 µm) (ex-device) | 43.31 | 38.99 | 27.52 | 42.39 | 28.59 |

TABLE 22-continued

| RPL554 Variant | SF | HC | ED | HB |
|---|---|---|---|---|
| Recovered RPL554 base/Capsule (ex-capsule) (µg) | 79.35 | 102.27 | 87.91 | 104.28 |
| Emitted Dose of RPL554 base/Capsule (ex-device) (µg) | 70.71 | 92.97 | 79.95 | 93.20 |
| FPF (% <5 µm) | 32.93 | 46.29 | 40.39 | 29.43 |
| MMAD (µm) | 2.10 | 1.72 | 1.96 | 2.31 |
| GSD | 2.69 | 2.42 | 2.42 | 2.24 |
| FPD RPL554 base (µg <5 µm) (ex-device) | 23.28 | 43.04 | 32.29 | 27.43 |

Key: FB—Free Base; ES—Ethanesulfonate; PT—p-Toluenesulfonate; MS—Methanesulfonate; BS—Benzenesulfonate; SF—Sulfate; HC—Hydrochloride; ED—Ethane-1,2-disulfonate; HB—Hydrobromide.

Particularly favourable fine particle fractions (FPFs) were observed for the hydrochloride and ethane-1,2-disulfonate salts.

Stability Assessment of Blends of RPL554 Variants: Lactose Powder Blends

No visible changes to the appearance of the powders were observed. In all cases except the sulfate salt, the peak area of the RPL554 from the different salt forms accounted for 96-99% of the total areas, after storage at both room and elevated temperatures. The sulfate salt showed only 82% of the total area, but this reflects the purity of the input material and is not suggestive of degradation. There does not appear to be any degradation caused by storage either at room temperature or at 70° C. for the free base or any of the salts.

The invention claimed is:

1. A pharmaceutically acceptable acid addition salt of:
   (i) 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one (RPL554); and
   (ii) ethane-1,2-disulfonic acid.

2. A pharmaceutically acceptable acid addition salt according to claim 1, which is RPL554 ethane-1,2-disulfonate.

3. A pharmaceutical composition comprising:
   (a) a pharmaceutically acceptable acid addition salt of (i) 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one (RPL554) and (ii) ethane-1,2-disulfonic acid; and
   (b) a pharmaceutically acceptable excipient, carrier or diluent.

4. A pharmaceutical composition according to claim 3, which is formulated for administration by inhalation.

5. A pharmaceutical composition according to claim 3, which is a dry powder.

6. A pharmaceutical composition according to claim 3, which is produced by dissolving a pharmaceutically acceptable acid addition salt of (i) 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one (RPL554) and (ii) ethane-1,2-disulfonic acid.

7. A pharmaceutical composition according to claim 6, wherein the aqueous solution is a buffered aqueous solution.

8. A pharmaceutical composition according to claim 7, wherein the buffered aqueous solution comprises a phosphate buffer, a citrate buffer or a citro-phosphate buffer.

9. A pharmaceutical composition according to claim 6, wherein the pH of the pharmaceutical composition is greater than or equal to about 2.5.

10. A pharmaceutical composition according to claim 6, wherein the pharmaceutically acceptable acid addition salt is present at a concentration of greater than or equal to about 1.0 mg/ml.

11. A method of treating or preventing a disease or condition selected from asthma, allergic asthma, hay fever, allergic rhinitis, bronchitis, emphysema, bronchiectasis, chronic obstructive pulmonary disease (COPD), adult respiratory distress syndrome (ARDS), steroid resistant asthma, severe asthma, paediatric asthma, cystic fibrosis, lung fibrosis, pulmonary fibrosis, interstitial lung disease, skin disorders, atopic dermatitis, psoriasis, ocular inflammation, cerebral ischaemia, inflammatory diseases and auto-immune diseases in a subject, which method comprises administering to said subject an effective amount of a pharmaceutically acceptable acid addition salt of (i) 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one (RPL554) and (ii) ethane-1,2-disulfonic acid.

12. A method of treating or preventing a disease or condition according to claim 11, wherein the disease or condition is chronic obstructive pulmonary disease (COPD).

* * * * *

UNITED STATES PATENT AND TRADEMARK OFFICE
CERTIFICATE OF CORRECTION

PATENT NO. : 10,463,665 B2
APPLICATION NO. : 15/549500
DATED : November 5, 2019
INVENTOR(S) : Peter Lionel Spargo et al.

It is certified that error appears in the above-identified patent and that said Letters Patent is hereby corrected as shown below:

In the Claims

In Claim 6, Column 35, Line 29:
"(ii) ethane-1,2-disulfonic acid." should read --(ii) ethane-1,2-disulfonic acid in an aqueous solution.--

Signed and Sealed this
Seventeenth Day of December, 2019

Andrei Iancu
*Director of the United States Patent and Trademark Office*